(12) United States Patent
Wechter

(10) Patent No.: US 6,555,575 B2
(45) Date of Patent: *Apr. 29, 2003

(54) USE OF γ-TOCOPHEROL AND ITS OXIDATIVE METABOLITE LLU-α IN THE TREATMENT OF DISEASE

(75) Inventor: William J. Wechter, Redlands, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/134,140

(22) Filed: Apr. 26, 2002

(65) Prior Publication Data

US 2002/0165268 A1 Nov. 7, 2002

Related U.S. Application Data

(63) Continuation of application No. 09/814,330, filed on Mar. 21, 2001, now Pat. No. 6,410,589, which is a continuation of application No. 09/461,645, filed on Dec. 14, 1999, now Pat. No. 6,242,479, which is a continuation of application No. 09/215,608, filed on Dec. 17, 1998, now Pat. No. 6,048,891.

(51) Int. Cl.[7] .................... A61K 31/35; A61K 31/355

(52) U.S. Cl. ........................ 514/456; 514/458

(58) Field of Search ................. 514/456, 458

(56) References Cited

U.S. PATENT DOCUMENTS

| | | | |
|---|---|---|---|
| 4,321,270 A | 3/1982 | Sundeen | 424/267 |
| 4,914,197 A | 4/1990 | Yamamoto et al. | 536/117 |
| 5,139,796 A | 8/1992 | Barkalow et al. | 426/3 |
| 5,200,214 A | 4/1993 | Barkalow et al. | 426/3 |
| 5,270,060 A | 12/1993 | Foster et al. | 426/3 |
| 5,739,156 A | 4/1998 | Bissett | 514/458 |
| 6,048,891 A | 4/2000 | Wechter | 514/456 |
| 6,242,479 B1 * | 6/2001 | Wechter | 514/456 |
| 6,426,362 B1 | 7/2002 | Miller et al. | 514/458 |
| 2002/0040053 A1 | 4/2002 | Kondo et al. | |
| 2002/0132845 A1 | 9/2002 | Miller et al. | 514/458 |
| 2002/0143049 A1 | 10/2002 | Miller et al. | 514/458 |

FOREIGN PATENT DOCUMENTS

| | | |
|---|---|---|
| EP | 0 326 987 A2 | 1/1989 |
| EP | 0 413 668 A2 | 8/1990 |
| WO | WO 96/05191 | 2/1996 |
| WO | WO 96/19215 | 6/1996 |

OTHER PUBLICATIONS

Murray, David E. et al. "Endogenoγus Natriuretic Factors 7: Biospecificity of a Natriuretic γ–Tocopherol Metabolite LLU–α[1]." The Journal of Pharmacology and Experimental Therapeutics, vol. 282, pp. 657–662 (1997).

Benaksas, et al., Life Sciences, 52:1045–54, 1993, "Endogenous Natriuretic Factors 1: Sodium Pump Inhibition does not Correlate with Natriuretic or Pressor Activities from Uremic Urine".

Bottje, et al., Poultry Science, 76:1506–12, Abstract Only, 1997, "Effect of Dietary dl–aplha–Tocopherol on Tissue alpha– and gamma–Tocopherol and Pulmonary Hypertension Syndrome (Ascities) in Broilers".

Campo, et al., Free Radical Biology and Medicine, "Reduction of Myocardial Infarct Size in rat by IRFI–048, a selective analogue of Vitamin E", vol. 16, pp. 427–435 (1994).

Campo, et al., Pharmacology, "Protective Effects of IRF–016, a New Antioxidant Agent, in Myocardial Damage, following coronary artery occlusion and reperfusion in the rat", 48:157–166 (1994).

Campo, et al., Research Comm. in Chem. Pathology and Pharmacology, "IRFI–016, a new radical scavenger, limits ischemic damage following coronary artery occlusion in rats", vol. 76, No., pp. 287–303, (1992).

Christen, et al., Proc. Natl. Acad. Sci. USA, 94(7):3217–22, Apr. 1997, "γ–Tocopherol Traps Mutagenic Electrophiles such as $NO_x$ and Complements α–Tocopherol: Physiological Implications".

Elson, Charles E., Chapter 39, Vitamine E in Health and Disease, Packer & Fuchs eds, Copyright 1993, pp. 533–545, "Impact of Palm Oil on Experimental Carcinogenesis".

Frei & Ames, Chapter 10, Vitamine E in Health and Disease, Packer & Fuchs eds, Copyright 1993, pp. 131–139, "Relative Importance of Vitamine E in Antiperoxidative Defenses in Human Blood Plasma and Low–Density Lipoprotein (LDL)".

Germano, Carl, http://www.solgar.com/nutrition_library/articles/tocotrienols.html, Posted Nov. 17, 1997, 4 pgs, "Tocotrienols in Health & Disease: A Novel Antioxidant in the Treatment of Hypercholesterolemia and Cancer".

Kantoci, et al., Journal of Pharmacology and Experimental Therapeutics, 282(2):648–656, 1997, "Endogenous Natriuretic Factors 6: The Stereochemistry of a Natriuretic γ–Tocopherol Metabolite LLU–α".

Life Extension Foundation, http://lef.org/prod_desc/item564.html, Copyright 1995–1999, 2 pgs., "Gamma E Tocopherol Formula".

(List continued on next page.)

Primary Examiner—Raymond Henley, III
(74) Attorney, Agent, or Firm—Knobbe, Martens, Olson & Bear, LLP

(57) ABSTRACT

The present invention is generally related to the discovery of the therapeutic benefit of administering γ-tocopherol and γ-tocopherol derivatives. More specifically, the use of γ-tocopherol and racemic LLU-α, (S)-LLU-α, or γ-tocopherol derivatives as antioxidants and nitrogen oxide scavengers which treat and prevent high blood pressure, thromboembolic disease, cardiovascular disease, cancer, natriuretic disease, the formation of neuropathological lesions, and a reduced immune system response are disclosed.

3 Claims, No Drawings

OTHER PUBLICATIONS

Life Extension Foundation, http://lef.org/cgi–local/shop.pl/page=feb98_newproduct.html, , Copyright 1995–1999, 3 pgs., "Not All Vitamin E is Created Equal".

McLaughlin, & Weihrauch, *Journal of the American Dietetic Association,* 75:647–665, Dec. 1979, "Vitamin E Content of Foods".

Meydani, Mohsen, *The Lancet,* 345:170–175, Jan. 21, 1995, "Vitamin E".

Meydani, S. & R. Tengerdy, Chapter 40, Vitamine E in Health and Disease, Packer & Fuchs eds, Copyright 1993, pp. 549–561, "Vitamin E and Immune Response".

Nando.net & The Associated Press, http://www.nando.net/newsroom/ntn/health/033197/health12_4931.html, Copyright 1997, 2 pgs., "Too Much Vitamin E Can be Harmful".

Packer, et al., Chapter 34, Vitamine E in Health and Disease, Packer & Fuchs eds, Copyright 1993, pp. 465–471, "Significance of Vitamin E for the Athlete".

Richardson P. & M. Steiner, Chapter 24, Vitamine E in Health and Disease, Packer & Fuchs eds, Copyright 1993, pp. 297–311, "Adhesion of Human Platelets Inhibited by Vitamin E".

Shigenaga, et al., *Proc. Natl. Acad. Sci. USA,* 94(7):3211–3216, Apr. 1997, "Inflammation and $NO_x$–induced Nitration: Assay for 3–nitrotyrosine by HPLC with Electrochemical Detection".

Speek, et al., *Journal of Food Science,* 501:121–124, 1985, "Vitamin E Composition of Some Speed Oils as Determined by High–Performance Liquid Chromatography with Fluorometric Detection".

Wechter, et al., *Proc. Natl. Acad. Sci. USA,* 93:6002–6007, Jun. 1996, "A New Endogenous Natriuretic Factor: LLU–α".

Weichet, et al., *Collection Czechoslov. Chem. Commun.,* 24:1689–1694, 1959, No Translation "Studien in der Gruppe der Vitamine K und E vi. Über die Darstellung von 2,5,7,8–Tetramethyl–2–(β–Carboxy–Äthyl)–6–Hydroxychroman und Dessen Oxydationsprodukt".

Official Monographs, USP 23, pp. 1631–1633, "Vitamin E," "Vitamin E Preparation," and "Vitamin E Capsules." No date available.

Burnett, et al., "Mechanisms of Phytochemical Inhibition . . . ," American Chemical Society Symposium Series, pp. 45–58, 1998.

Stone, et al., "Tocopherols and the Etiology of Colon Cancer," Journal of the National Cancer Institute, vol. 89, pp. 1006–1014, 1997.

Beharka, et al., "vitamin E Status and Immune Function," Methods in Enzymology, vol. 282, pp. 247–263, 1997.

Odeleve, et al., "The Potential Role of Vitamin E in the Treatment of Immunologic Abnormalities During Acquired Immune Deficiency Syndrome," Database Medline, 1991.

Yarita, et al., "Supercritical Fluid Chromatographic Determination of Cholesterol and Cholesteryl Esters in Serum on ODS–Silica Gel Column," Journal of Chromatography A., vol. 679, pp. 329–334, 1994.

The Merck Index, $11^{th}$ edition, published by Merck & Col., Inc. (NJ), 1989, citation 9418, p. 1495.

* cited by examiner

USE OF γ-TOCOPHEROL AND ITS OXIDATIVE METABOLITE LLU-α IN THE TREATMENT OF DISEASE

CROSS-REFERENCE TO RELATED APPLICATIONS

This application is a continuation of U.S. patent application Ser. No. 09/814,330, filed Mar. 21, 2001, now U.S. Pat. No. 6,410,589, which is a continuation application of U.S. patent application Ser. No. 09/461,645, filed Dec. 14, 1999, now U.S. Pat. No. 6,242,479, issued Jun. 5, 2001, which is a continuation application of U.S. patent application Ser. No. 09/215,608, filed Dec. 17, 1998, now U.S. Pat. No. 6,048,891, issued Apr. 11, 2000. All of these prior applications which are hereby expressly incorporated by reference in their entireties.

FIELD OF INVENTION

The present invention is generally related to the discovery of the therapeutic benefit of administering γ-tocopherol and γ-tocopherol derivatives. More specifically, the use of γ-tocopherol and racemic LLU-α, (S)-LLU-α, or other γ-tocopherol derivatives as antioxidants and nitrogen oxide scavengers which treat and prevent high blood pressure, thromboembolic disease, cardiovascular disease, cancer, natriuretic disease, the formation of neuropathological lesions, and a reduced immune system response are disclosed.

BACKGROUND OF THE INVENTION

Vitamin E, an essential fat-soluble vitamin, encompasses eight naturally occurring compounds in two classes. The first class, tocopherols, have four members designated alpha, beta, gamma and delta. The two major forms, α-tocopherol and γ-tocopherol, differ structurally only by a methyl group substitution at the 5-position. The second class, tocotrienols, are molecules related to the tocopherols and also consist of four members designated alpha, beta, gamma and delta. The tocotrienol structure differs from the tocopherols by possessing three double bonds in their side chain rather than being saturated.

One of the important chemical features of the tocopherols is that they are redox agents which act under certain circumstances as antioxidants. In acting as an antioxidant, tocopherols presumably prevent the formation of toxic oxidation products, such as peroxidation products formed from unsaturated fatty acids. Early on, investigators attributed most if not all of the biological activity of the tocopherols to their ability to act as antioxidants. More recently, however, other biological activities have been associated with tocopherols including the modulation of signal transduction, modulation of phospholipid metabolism, inhibition of protein kinase C, inhibition of phospholipase A and inhibition of prostaglandin production. (Meydani and Mosen, *The Lancet* 345(8943):170–175 (1995)).

Further, it has recently been discovered that individual members in the class of tocopherols may exhibit different biological properties from one another despite their structural similarity. Some investigators, for example, believe that γ-tocopherol, unlike α-tocopherol, acts in vivo as a trap for membrane-soluble electrophilic nitrogen oxides and other electrophilic mutagens. (Christen et al. *Proc. Natl. Acad. Sci.* 94: 3217–3222 (1997)). In contrast, others report that α-tocopherol is a more powerful antioxidant and has ten times the biological activity of γ-tocopherol. (Meydani and Mosen, *The Lancet* 345(8943):170–175 (1995)). Alpha-tocopherol is also thought to be retained in the body longer than γ-tocopherol and has been shown to preferentially reincorporate into nascent very low-density lipoproteins (LDL). (Christen et al. *Proc. Natl. Acad. Sci.* 94: 3217–3222 (1997)). At present, an understanding of the differences in biological activity of the four tocopherols and their effect on the body is in its infancy.

Alpha tocopherol is largely considered the most important member of the class of tocopherols because it constitutes about 90% of the tocopherols found in animal tissues and displays the greatest biological activity in the commonly used bioassay systems. In consequence, vitamin E supplements are almost exclusively made of α-tocopherol and little investigation into the efficacy of supplementation with γ-tocopherol has been conducted.

The therapeutic benefits of vitamin E supplementation remains a subject of considerable debate. Several studies have proposed that vitamin E supplementation may prevent a plethora of ills but many of these studies fail to provide causal connections between vitamer supplementation and therapeutic benefit; they merely indicate that a high dietary or plasma concentration and supplemental intake of vitamin E is associated with a reduced risk of disease. In fact, some studies have failed to demonstrate that tocopherol supplementation provides any protection from disease. (Meydani and Mosen, *The Lancet* 345(8943): 170–175 (1995) and (Christen et al. *Proc. Natl. Acad. Sci.* 94: 3217–3222 (1997)). A reliable method to treat and prevent diseases associated with oxidative stress and vitamin E deficiency is highly desirable.

SUMMARY OF THE INVENTION

The present invention reveals the discovery of the therapeutic benefit of administering γ-tocopherol and γ-tocopherol derivatives such as LLU-α. The novel use of γ-tocopherol and γ-tocopherol derivatives as antioxidants and nitrogen oxide scavengers which treat and prevent high blood pressure, thromboembolic disease, cardiovascular disease, cancer, natriuretic disease, the formation of neuropathological lesions, and a reduced immune system response are disclosed.

One embodiment of the present invention is a medicament comprising γ-tocopherol and LLU-α with and without additional active ingredients that are effective in producing a natriuretic effect. Another embodiment is a medicament comprising γ-tocopherol, α-tocopherol, and LLU-α with and without additional active ingredients that are effective in producing a natriuretic effect. A further embodiment is a medicament comprising γ-tocopherol, β-tocopherol, and LLU-α, with and without additional active ingredients that are effective in producing a natriuretic effect. Still further, an embodiment comprising α-tocopherol, γ-tocopherol, β-tocopherol, and LLU-α, with and without additional active ingredients that are effective in producing a natriuretic effect, is disclosed. In the alternative, the embodiments described above may include (S)-LLU-α or other γ-tocopherol derivatives instead of LLU-α.

According to the methods of treatment and prevention disclosed, the medicaments described above are administered to subjects suffering from high blood pressure, thromboembolic disease, atherosclerosis, cardiovascular disease, cancer, natriuretic disease, the formation of neuropathological lesions, and a reduced immune system response. One method involves the administration of a therapeutically beneficial amount of γ-tocopherol, with or without supplementation of LLU-α, to subjects suffering from a high blood pressure so as to treat and prevent this condition. By another method, a therapeutically beneficial amount of γ-tocopherol, with or without supplementation of LLU-α, is administered to treat and prevent thromboembolic disease. A related method to treat and prevent the aggregation of platelets and/or binding of platelets to adhesive proteins is also disclosed.

Another method contemplated by the present inventor involves the administration of a therapeutically beneficial amount of γ-tocopherol, with or without supplementation of LLU-α, to treat and prevent cardiovascular diseases, such as ischemia, angina, edematous conditions, artherosclerosis, LDL oxidation, adhesion of monocytes to endothelial cells, foam-cell formation, fatty-streak development, platelet adherence, platelet aggregation, smooth muscle cell proliferation, and reperfusion injury. Further, a method to treat and prevent cancers, such as lung cancer, prostate cancer, breast cancer, and colon cancer by administering a therapeutically beneficial amount of γ-tocopherol, with or without supplementation of LLU-α are presented.

Methods of treatment and prevention of natriuretic diseases, such as hypertension, high blood pressure, ischemia, angina pectoris, congestive heart failure, cirrhosis of the liver, nephrotic syndrome, ineffective renal perfusion, or ineffective glomerular filtration, by administering a therapeutically beneficial amount of γ-tocopherol, with or without supplementation of LLU-α are also provided. Additionally, methods of treating and preventing neurological diseases including hyporeflexia, opthalmoplegia, and axonal dystrophy using a therapeutically beneficial amount of γ-tocopherol, with or without supplementation of LLU-α, are described. Finally, methods to improve a subject's immune system response and a related method to reduce the production of free-radicals by administering a therapeutically beneficial amount of γ-tocopherol, with or without supplementation of LLU-α, is revealed.

CHEMICAL STRUCTURE OF LLU-α
FORMULA A shows the structural formula of LLU-α.

(formula A)

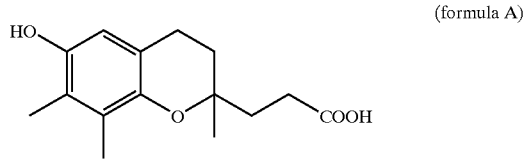

FORMULA B shows the structural formula of (S)-LLU-α.

(formula B)

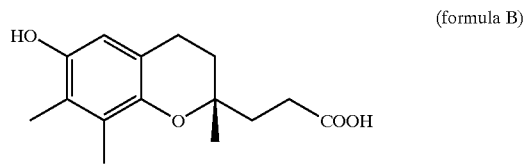

DETAILED DESCRIPTION OF THE PREFERRED EMBODIMENTS

In accordance with the present invention, a novel method for the treatment and prevention of high blood pressure, thromboembolic disease, atherosclerosis, cancer, natriuretic disease, the formation of neuropathological lesions, and a reduced immune system response is provided. The method involves administering orally or parenterally substantially pure γ-tocopherol or a formulation comprising γ-tocopherol and racemic LLU-α, (S)-LLU-α, or other γ-tocopherol derivative.

By "LLU-α" is meant the compound 6-hydroxy-2,7,8-trimethylchroman-2-propanoic acid, molecular weight of 264.1362 and molecular formula of $C_{15}H_{20}O_4$. LLU-α may be in the racemic form or as the S enatiomer (also denoted as (S)-LLU-α). A general discussion of the isolation and characterization of LLU-α is provided by Wechter et al. (U.S. patent application Ser. No. 08/290,430) the disclosure of which is hereby incorporated by reference.

By "γ-tocopherol derivative" is meant γ-tocopherol metabolites and synthetic chroman derivatives including, but not limited to, LLU-α, LLU-γ, racemic chromans, chroman methyl esters, chroman esters, chroman amides, $R_4$ chroman esters, oxidized chroman derivatives, racemic 2,5,7,8-tetramethyl-2-(β-carboxyethyl)-6-hydroxy chroman, 2,5,7,8-tetramethyl-2-(β-carboxyethyl)-chroman, 2,7,8-trimethyl-2-(β-carboxyethyl) chroman, racemic 4-methyl-6-(5,6-dimethylbenzohinoyl)-4-hexanolid, 4-Methyl-6-(3,5,6-trimethylbenzochinoyl)-4-hexanolid, (S)-4-Methyl-6-(5,6-dimethylbenzochinoyl)-4-hexanolid, 2,7,8-Trimethyl-2-(β-carboxyethyl)-6-acetyl chroman, 2,7,8-Trimethyl-2-(β-carboxyethyl)-6-acetyl chroman methyl ester, and benzodipyran methyl ester. Many γ-tocopherol derivatives are natriuretic compounds but the meanining of "γ-tocopherol derivative" is not intended to be limited to only natriuretic compounds. Other γ-tocopherol metabolites and synthetic chroman derivatives may be known by those of skill in the art or will be discovered in the future and are encompassed by this definition.

By "natriuretic disease" is meant diseases associated with abnormal excretion of sodium from the body. The term natriuretic disease includes but is not limited to hypertension, high blood pressure, ischemia, angina pectoris, congestive heart failure, cirrhosis of the liver, nephrotic syndrome, ineffective renal perfusion, and ineffective glomerular filtration, or any combination thereof. Other forms of natriuretic disease will be apparent to those of skill in the art and are encompassed by the definition as used in this invention.

As used herein, the term "natriuretic compound" refers to a compound which increases the rate of sodium excretion without contributing to significant potassium loss in a mammal upon administering the compound to the mammal. The term "natriuretic compound" also refers to both the native compound and in vitro or in vivo modifications which retain natriuretic activity. It is understood that limited modifications, substitution or deletions of functional groups may be made without destroying the biological activity. Moreover, it will be recognized by those skilled in the arts of chemistry and pharmaceutical preparation that many derivatives can be made which are biologically and chemically equivalent to, or even more active than, the indicated compounds hereinafter. Examples of equivalent compounds include esters, ethers, amides and salts of the foregoing compounds.

"Substantially purified," when used to describe the state of the natriuretic compound, denotes the compounds essentially free of proteins, steroids, and other material normally associated or occurring with natriuretic compounds in its native environment.

As used herein, the term "post salt peak" refers to material eluted from a G-25 Sephadex column which appears immediately after the sodium, potassium, urea and creatinine containing fractions which has uv. absorbance at 290 nm.

A material is "biologically active" if it is capable of increasing natriuresis in an in vivo assay as described herein.

By "thromboembolic disease" is meant diseases characterized by platelet aggregation, platelet adhesion to adhesive proteins, or platelet hyperactivity. Although thromboembolic disease is commonly associated in insulin-dependent diabetic patients, this understanding is not intended to limit the invention. Elderly patients and patients suffering from various forms of cardiovascular disease exhibit platelet aggregation, platelet adhesion to adhesive proteins, and platelet hyperactivity which can be defined as forms of thromboembolic disease for the purposes of this invention. Other forms of thromboembolic disease will be apparent to those of skill in the art and are encompassed by the definition used in this invention.

By "cardiovascular disease" is meant diseases associated with the cardio-pulmonary and circulatory systems including but not limited to ischemia, angina, edematous conditions, artherosclerosis, LDL oxidation, adhesion of monocytes to endothelial cells, foam-cell formation, fatty-streak development, platelet adherence, and aggregation, smooth muscle cell proliferation, reperfusion injury, and other conditions known by those of skill in the art to be related to the pathogenesis of cardiovascular disease.

By "cancer" is meant diseases that have been associated with mutagenesis, cell transformation, oncogenesis, neoplasia, or metastasis, including but not limited to, various forms of lung cancer, prostate cancer, breast cancer, and colon cancer, or any combination thereof. Other forms of cancer will be apparent to those of skill in the art and are encompassed by the definition used in this invention.

By "neurological disease" is meant diseases associated with the brain and nervous system, including but not limited to, hyporeflexia, proprioception, opthalmoplegia, and axonal dystrophy. Other forms of neurological diseases will be apparent to those of skill in the art and are encompassed by the definition as used in this invention.

Gamma-tocopherol is a water-insoluble, non swelling amphiphile, as are triglycerides and cholesterol. Thus, many of the processes involved in the absorption of lipids are also required for absorption of γ-tocopherol such as emulsification, solubilization within mixed bile salt micelles, uptake by the small intestine, packaging within lipoprotein particles, and secretion into the circulation via the lymphatic system. Gamma-tocopherol is transferred to tissues in much the same manner as other lipids and spontaneous transfer and exchange of tocopherol between cell membranes has been documented. Since γ-tocopherol is rapidly absorbed in the lipids of various tissues including the liver, its antioxidant and radical scavenger activities primarily occur in the lipid phase and only tangentially in the aqueous phase. LLU-α, on the other hand, is considerably more hydrophilic than γ-tocopherol and acts as an antioxidant, a natriuretic compound, and radical scavenger in primarily the aqueous phase. Thus, the present inventor contemplates a method to treat and prevent disease which employs supplements comprising γ-tocopherol with and without fortification with racemic LLU-α, (S)-LLU-α, or other γ-tocopherol derivative so as to selectively provide natriuretic redox agents to the lipid and aqueous phases of a patient's body.

The preparation of soft gelatin capsules comprising commercially available γ-tocopherol in doses of 200 to 800 mg is understood by those of skill in the art. The γ-tocopherol may be present as the free alcohol or the acetate or succinate ester. A supplement of γ-tocopherol preferably contains at least 60–65% (weight to weight) γ-tocopherol and up to 10% α-tocopherol and 25% β-tocopherol as isolated from soy oil, or in certain circumstances up to 25% δ-tocopherol. Particularly preferred compositions include at least 70% γ-tocopherol. These formulations are only intended to guide one of skill in the art and formulations of γ-tocopherol that would be effective for use in the disclosed methods may include as low as 50% (weight to weight) γ-tocopherol or up to 100% (weight to weight) γ-tocopherol, but desirably contain 55% (weight to weight) γ-tocopherol to 95% (weight to weight) γ-tocopherol.

In another embodiment of this invention, soft gelatin capsules comprising commercially available γ-tocopherol are fortified with a natriuretic compound such as LLU-α, (S) LLU-α, or other γ-tocopherol derivative some of which may be present as the free acid or a simple ester. One aspect of the invention, for example, comprises a natriuretic compound having the formula I:

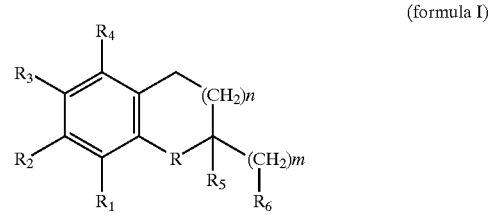

(formula I)

in which

R is O, S, SO, $SO_2$, a secondary or tertiary amine group, a phosphate group, a phosphoester group, or an unsubstituted or substituted methylene group, $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, $R_3$ and $R_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, $R_5$ is H, OH, alkyl, aryl, alkenyl, alkynyl, aromatic, ester or unsubstituted or substituted amine, $R_6$ is COOH, $COOR_7$, $CONH_2$, $CONHR_7$, $CONR_7R_8$, $NH_2$, $NHR_7$, $NR_7R_8$, or a carboxylate salt, $R_7$ and $R_8$ independently are unsubstituted or substituted alkyl, aryl, alkaryl, aralkyl, alkenyl or alkynyl, n is 0 to 3, and m is 0 to 5.

As used herein, the term "substituted" denotes the presence of one or more substituent such as alkyl, aryl, alkaryl, aralkyl, ether or halogen. More particular substituents include $C_{1-6}$ unbranched or branched alkyl, such as methyl, ethyl, propyl, n-butyl, sec-butyl and tert-butyl, and $C_{6-12}$ aryl, particularly phenyl.

In a preferred embodiment, R is O. Also preferably, n=1. Preferably, m=2.

$R_6$ preferably is COOH.

Preferably, $R_3$ is H or OH. Also preferably, $R_4$ is H or $CH_3$.

In a preferred embodiment, $R_1$, $R_2$ and $R_5$ are $CH_3$.

Exemplary preferred compounds of formula I include those in which R is O, $R_1$, $R_2$ and $R_5$ are $CH_3$, $R_3$ is OH, $R_4$ is H or $CH_3$, $R_6$ is COOH, n=1 and m=2.

Other exemplary preferred compounds of formula I includes those in which R is O, $R_1$, $R_2$ and $R_5$ are $CH_3$, $R_3$ is H, $R_4$ is H or $CH_3$, $R_6$ is COOH, n=1 and m=2.

In a preferred embodiment, $R_7$ is a $C_{1-6}$ alkyl group, in particular $CH_3$.

In another preferred embodiment, $R_3$ is OH.

Compounds used in the present invention can also be obtained by modifying the above recited formula in numerous ways while preserving natriuretic activity. Examples of such active derivatives include compounds of formulae II–V, below.

In all formulae described herein, moieties having like designations are considered to correspond to each other as like moieties in related compounds.

Another aspect of the invention comprises natriuretic compounds having the formula II:

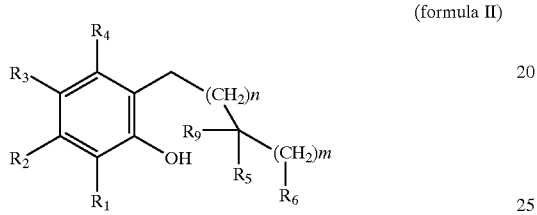

(formula II)

wherein $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, $R_3$ and $R_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, $R_5$ is H, OH, alkyl, aryl, alkenyl, alkynyl, aromatic, ester or unsubstituted or substituted amine, $R_6$ is COOH, $COOR_7$, $CONH_2$, $CONHR_7$, $CONR_7R_8$, $NH_2$, $NHR_7$, $NR_7R_8$, or a carboxylate salt, $R_7$ and $R_8$ independently are unsubstituted or substituted alkyl, aryl, alkaryl, aralkyl, alkenyl or alkynyl, $R_9$ is hydroxyl or unsubstituted or substituted alkoxyl, n is 0 to 3, and m is 0 to 5.

In a preferred embodiment, $R_1$, $R_2$ and $R_5$ are $CH_3$. Preferably, $R_3$ is OH.

$R_4$ preferably is H.

Additionally, it is preferred that n=1. Preferably m=2.

In a preferred embodiment, $R_6$ is $COOCH_2CH_3$ and $r_9$ is OH. In another preferred embodiment, $R_6$ is COOH and $R_9$ is $CH_3CH_2O$.

Specific examples includes the following:

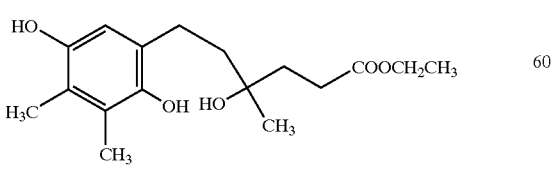

(formula IIa)

A further aspect of the invention comprises natriuretic compounds having the formula III:

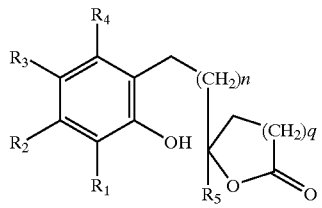

(formula III)

wherein $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, $R_3$ and $R_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, $R_5$ is H, OH, alkyl, aryl, alkenyl, alkynyl, aromatic, ester or unsubstituted or substituted amine, n is 0 to 3, and q is 0 to 4.

In preferred embodiments, n=1. Also preferred are compounds in which m=2.

Exemplary natriuretic compounds of formula III include the following:

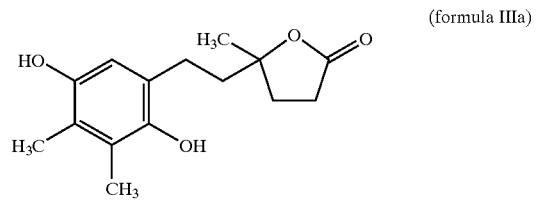

(formula IIIa)

The instant invention comprises other natriuretic compounds having the formula IV:

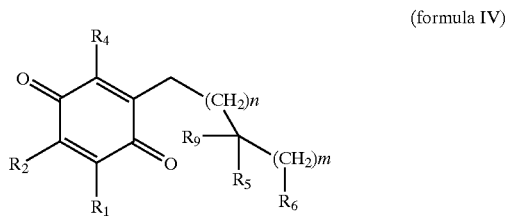

(formula IV)

wherein $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, $R_4$ is H, OH, alkyl, aryl, alkenyl, alkynyl, aromatic, ether, ester, unsubstituted or substituted amine, amide, halogen or unsubstituted or substituted sulfonyl, $R_5$ is H, OH, alkyl, aryl, alkenyl, alkynyl, aromatic, ester or unsubstituted or substituted amine, $R_6$ is COOH, $COOR_7$, $CONH_2$, $CONHR_7$, $CONR_7R_8$, $NH_2$, $NHR_7$, $NR_7R_8$, or a carboxylate salt, $R_7$ and $R_8$ independently are unsubstituted or substituted alkyl, aryl, alkaryl, aralkyl, alkenyl or alkynyl, $R_9$ is hydroxyl or unsubstituted or substituted alkoxyl, n is 0 to 3, and m is 0 to 5.

Preferably n=1. Also, preferably m=2.

Specific compounds of the invention according to formula IV include:

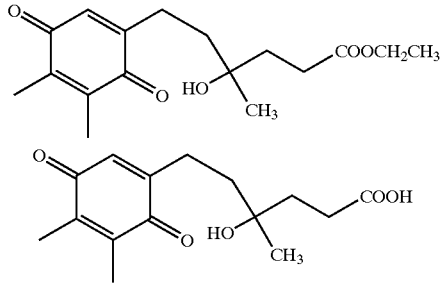
(formula IVa)

Natriuretic compounds of formula V are also combined with γ-tocopherol to make the medicaments of the instant invention:

(formula V)

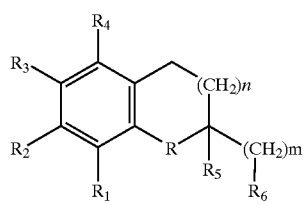

wherein $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, $R_4$ is H, OH, alkyl, aryl, alkenyl, alkynyl, aromatic, ether, ester, unsubstituted or substituted amine, amide, halogen or unsubstituted or substituted sulfonyl, $R_5$ is H, OH, alkyl, aryl, alkenyl, alkynyl, aromatic, ester or unsubstituted or substituted amine, n is 0 to 3, and q is 0 to 4.

Preferred embodiments are those in which n=1. Also, it is preferred that m=2.

Included in the inventive compounds of formula V are:

(formula Va)

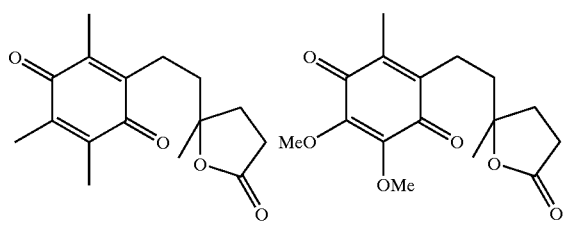

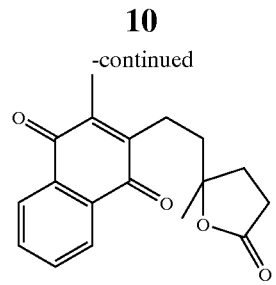

In accordance with another aspect of present invention, medicaments having the formula Ia and γ-tocopherol are contemplated.

(formula Ia)

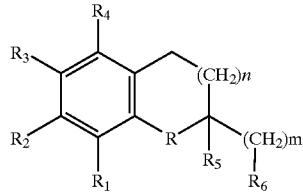

in which

R is O, S, SO, $SO_2$, a secondary or tertiary amine group, a phosphate group, a phosphoester group, or an unsubstituted or substituted methylene group, $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, $R_3$ and $R_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, $R_5$ is H, OH, alkyl, aryl, alkenyl, alkynyl, aromatic, ester or unsubstituted or substituted amine, $R_6$ is COOH, $COOR_7$, $CONH_2$, $CONHR_7$, $CONR_7R_8$, $NH_2$, $NHR_7$, $NR_7R_8$, or a carboxylate salt, $R_7$ and $R_8$ independently are unsubstituted or substituted alkyl, aryl, alkaryl, aralkyl, alkenyl or alkynyl, n is 0 to 3, and m is 0 to 5.

In preferred embodiments, (i) when R is O, R, $R_2$ and $R_5$ are $CH_3$, $R_3$ and $R_6$ are OH, and $R_4$ is H, m=2 to 5;

(ii) when R is O $R_1$ is H or $CH_3$, $R_2$ is H, $CH_3$, $C(CH_3)_3$ or $CH(CH_3)_2$, $R_3$ is OH or $CH_3COO$, $R_4$ is $CH_3$ or $CH(CH_3)_2$, $R_5$ is H, $CH_3$ or $CH_2CH_3$, and $R_6$ is H, OH, $OCH_3$, $OCH_2CH_3$ or $NH_2$, m=1 to 5;

(iii) when R is O, $R_1$ and $R_5$ are $CH_3$, $R_2$ and $R_4$ are H, $R_3$ is OH or $CH_3COO$, and $R_6$ is OH or $CH_3O$, m is not 2;

(iv) when R is O, $R_1$, $R_2$ and $R_5$ are $CH_3$, $R_3$ is OH or $CH_3COO$, $R_4$ is alkyl having at least two carbon atoms, and $R_6$ is H, OH or ester, m=1; and (v) when $R_1$, $R_2$ and $R_5$ are methyl, $R_3$ and $R_6$ are OH and $R_4$ is alkyl, m=2.

Certain medicaments of the present invention comprise natriuretic compounds that have been isolated in substantially pure form. The natriuretic compounds are obtained from a variety of sources, including urine, hypothalamus, adrenal, liver, kidney, plasma, blood and cultured cells. Human uremic urine is the preferred source, although normal human urine or hypertensive human urine may also be used.

One of the isolated natriuretic compounds used to make a medicament of the present invention is LLU-α. LLU-α has the following properties: a major ultraviolet absorbance peak at about 210 nm; a broad secondary peak at about 295 nm; instability in dilute base; capability of esterification by reaction with $CH_2N_2$. The compound is capable of increasing sodium excretion in the urine in mammals without a corresponding increase in potassium excretion, and does not cause a significant change in mean arterial pressure. The compound additionally acts as a cardio-selective free radical scavenger.

Medicaments of the instant invention also comprise another isolated natriuretic compound, named LLU-γ, which has the following properties: a major ultraviolet absorbance peak at about 220 nm; a secondary peak at about 268 nm; high instability in the presence of $O_2$ or in dilute base. It is capable of increasing sodium excretion in mammalian urine without a corresponding increase in potassium excretion, although potassium excretion (kaliuresis) may be observed occasionally after infusion of the compound into conscious rats. In addition, it does not cause a significant change in mean arterial pressure and it shows no inhibition of the sodium pump.

Natriuretic compounds which comprise the present invention can be purified by a number of methods, particularly those exemplified herein. In a preferred method within the invention, collected urine is processed by ultrafiltration ($\leq 3$ kDa), gel filtration chromatography (G-25) and extraction with isopropanol and diethyl ether. The organic soluble material is then subjected to sequential high-performance liquid chromatography, while assaying for the natriuretic activity in vivo. Alternatively, collected urine is extracted with ether, separated by high performance liquid chromatography, and fractions are assayed for natriuretic activity.

In a further alternative embodiment, the natriuretic compounds in the medicaments of the present invention can be synthesized using methods known to those skilled in the art. One such method is the method described by J. Weichet et al., Czech. Chem. Commun. 24, 1689–1694 (1959), the disclosure of which is hereby incorporated by reference. This method can readily be adapted by one of ordinary skill in the art to provide a method of synthesizing the compounds of the present invention. Other methods to synthesize the natriuretic compounds of the present invention are disclosed in Wechter et al., *Proc. Natl. Acad. Sci. USA* 93:6002–6007 (1996) and Kantoci et al., *J. Pharmacology and Experimental Therapeutics* 282:648–656 (1997) which are hereby incorporated by reference.

A preferred synthetic method includes the step of reacting a compound of the formula VI:

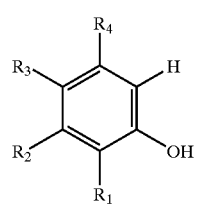

(formula VI)

in which

R_1 and R_2 independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, and R_3 and R_4 independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, with a vinyl lactone of the formula VII:

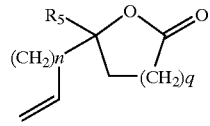

(formula VII)

in which

R_5 is H, alkyl, aryl, alkenyl, alkynyl, aromatic or ester, n is 0 to 3, and q is 0 to 4.

In a preferred embodiment of the foregoing synthesis, R_3 is OH. Preferably, R_4 is not simultaneously OH. A preferred compound of formula VI is a hydroquinone, for example 2,3-dimethyl-1,4-hydroquinone.

A preferred vinyl lactone of formula VII is γ-methyl-γ-vinylbutyrolactone (R_5=CH_3, n=1, q=1).

In carrying out the foregoing reaction, preferably a catalyst is used, such as a metallic or non-metallic salt. Specific types of catalyst include non-metallic salts which form complexes with a solvent, particularly a catalyst such as boron trifluoride diethyl etherate.

In carrying out the foregoing reaction, preferably an aprotic or protic solvent is employed, in particular an aprotic solvent such as dioxane. The catalyst and/or the vinyl lactone is preferably diluted in the selected solvent.

Preferably the synthesis is carried out at an elevated temperature, such as 100–110° C.

In a preferred embodiment, the foregoing reaction mixture is diluted with an aprotic or protic solvent, particularly an aprotic solvent such as diethyl ether.

The desired product preferably is obtained from concentrated supernatant which is purified, for example, using an RP-HPLC column or silica gel. Preferred eluents for RP-HPLC include mixtures of water, acetonitrile and acetic acid. Preferred solvents for silica gel include ethyl acetate and hexane. Other purification methods, such as crystallization, can be used. Also, other eluents, such as hexane and dimethyl ketone, can be employed.

The foregoing synthesis produces a racemic mixture, of which typically one enantiomer is active while the second enantiomer is less active or inactive. The racemate can be employed in compositions according to the invention, with adjustment of the quantity to account for the presence of the inactive enantiomer. Alternatively, the racemate can be resolved using conventional methods, and the active enantiomer identified and utilized. All enantiomeric forms of the compounds described herein are specifically contemplated as being within the scope of the instant invention.

As a byproduct of the foregoing synthesis, derivative compounds of formula VIII are produced:

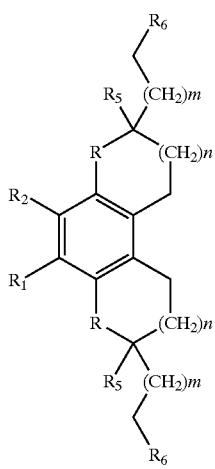

(formula VIII)

These compounds can also be employed as natriuretic compounds which comprise the medicamnet according to the instant invention. Exemplary compounds of formula VIII include the following benzodipyran derivatives:

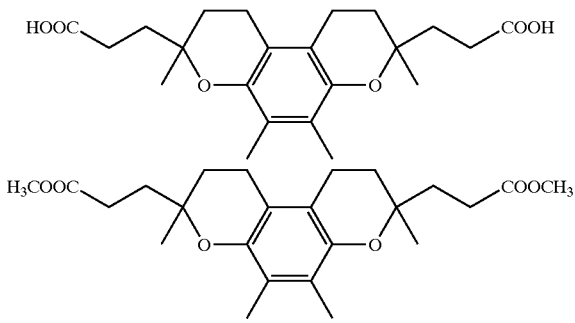

(formula VIIIa)

All stereoisomeric forms of the foregoing compounds, including meso compounds and diastereomeric pairs, are specifically contemplated as being within the scope of the instant invention.

Di-oxidized and/or di-hydrated derivatives of the compounds of formula VIII can be obtained in a manner analogous to those used to obtain compounds of formulae II–V from the compounds of formula I.

As mentioned previously, natriuretic compounds which comprise the medicamnets of the instant invention can be modified by formation of esters, amides, etc. Esterification can be carried out, for example, by reaction with a solution of a diazoalkane, or with an anhydride or an acyl chloride. Amides can be formed by reaction with ammonia or an amine.

Natriuretic compounds of formulae II–V can be derived from the corresponding natriuretic compounds produced by the foregoing method, for example, by oxidation. In a preferred embodiment of this process, when $R_4$=H, $R_5$ is not $CH_3$.

A preferred oxidizer for the foregoing method is a solution of ferric chloride. Other oxidants, such as $KMnO_4$, $SeO_2$, $CrO_3$, $H_2O_2$, m-chloroperbenzoic acid, Caro acid, $OsO_4$, $HIO_4$, potassium ferricyanide, silver chromate or sodium perborate, can also be used.

Scheme 1 illustrates the relationship between exemplary compounds of formulae I–V. Note that Scheme 1 depicts the relationships between the S-enantiomers. The same relationships exist between the corresponding R-enantiomers. A wide variety of natriuretic compounds within the scope of the instant invention can be obtained in the manner illustrated.

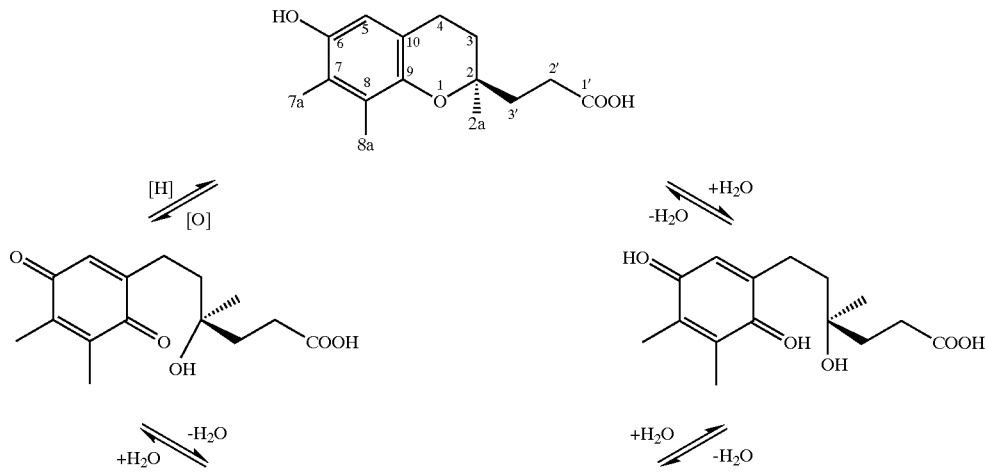

(Scheme 1)

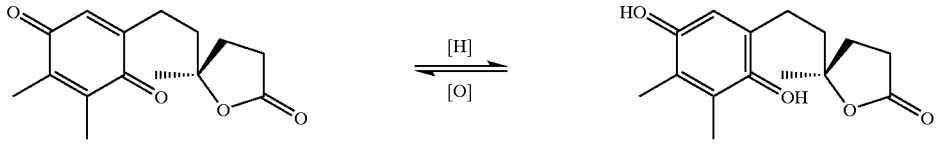

Formulations of medicaments comprising γ-tocopherol and LLU-α, (S)-LLU-α, or other γ-tocopherol derivatives, detailed above, are as follows. Racemic LLU-α is synthesized or isolated and may be present as the free acid or a simple ester. Racemic LLU-α is added to the differing concentrations of γ-tocopherol with or without a suitable filler. A supplement comprising γ-tocopherol and racemic LLU-α preferably contains 5% to 95% (weight to weight) γ-tocopherol mixed with 5% to 95% racemic LLU-α, and may also include other tocopherols. More preferably, the compositions of this embodiment of the invention include between 25% and 60% racemic LLU-α, or still more preferably no more than 50% (weight to weight) racemic LLU-α. A particularly preferred composition includes 26% (weight to weight) racemic LLU-α with the remaining amount of the supplement being composed of tocopherols and a suitable filler, with at least 65% of the tocopherols being γ-tocopherol.

Soft gelatin capsules comprising commercially available γ-tocopherol are fortified with (S)-LLU-α using the same compositions, above. (S)-LLU-α is synthesized or isolated, as detailed above or in the following examples, and may be present as the free acid or a simple ester. (S)-LLU-α is added to the formulations of the γ-tocopherol supplements mentioned above with or without a suitable filler. A supplement comprising γ-tocopherol and (S)-LLU-α preferably contains 5% to 95% (weight to weight) γ-tocopherol mixed with 5% to 95% (S)-LLU-α, and may also include other tocopherols. More preferably, the compositions of this embodiment of the invention include between 25% and 60% (S)-LLU-α, or still more preferably no more than 50% (weight to weight) (S)-LLU-α. A particularly preferred composition includes 26% (weight to weight) (S)-LLU-α with the remaining amount of the supplement being composed of tocopherols and a suitable filler, with at least 65% of the tocopherols being γ-tocopherol.

Alternatively, soft gelatin capsules comprising commercially available γ-tocopherol are fortified with a γ-tocopherol derivative. The γ-tocopherol derivative is synthesized or isolated, as detailed above or in the following examples, and may be present as the free acid or a simple ester. An γ-tocopherol derivative is added to the formulations of the γ-tocopherol supplements mentioned above with or without a suitable filler. A supplement comprising γ-tocopherol and a γ-tocopherol derivative preferably contains 5% to 95% (weight to weight) γ-tocopherol mixed with 5% to 95% γ-tocopherol derivative, and may also include other tocopherols. More preferably, the compositions of this embodiment of the invention include between 25% and 60% γ-tocopherol derivative, or still more preferably no more than 50% (weight to weight) γ-tocopherol derivative. A particularly preferred composition includes 26% (weight to weight) γ-tocopherol derivative with the remaining amount of the supplement being composed of tocopherols and a suitable filler, with at least 65% of the tocopherols being γ-tocopherol. Other tocopherols can be included in the formulations, including α-tocopherol, β-tocopherol and δ-tocopherol. In certain circumstances, δ-tocopherol can substitute for γ-tocopherol in the formulations and methods described herein.

The preferred method of administering principally γ-tocopherol or the formulation comprising γ-tocopherol and racemic LLU-α, (S)-LLU-α, or γ-tocopherol derivative is orally via soft gelatin capsules, however, several methods of administering these therapeutics would be within the skill of one in the art. Gamma-tocopherol or the formulations mentioned above can be administered neat, as mixtures with other physiologically acceptable active or inactive materials such as moistening agents, flavoring agents, binding agents, and extenders, as well as other compounds having pharmacological activities, such as other diuretics which increase the distal delivery of sodium, other anti-cancer therapeutics, other high blood pressure medicaments, other anti-hypertensive agents, or other mixtures of tocopherols. It may also be administered with physiologically suitable carriers such as, for example, olive oil, sesame oil, or other lipid. The compounds can be administered orally or parenterally, for example, by injection. Injection can be subcutaneous, intravenous, or by intramuscular injection.

The total daily dose of 200–800 mg can consist of a single individual dose or multiple doses given at intervals. Dosages within these ranges can also be administered by constant infusion over an extended period of time, usually exceeding 24 hours, until the desired therapeutic benefits have been obtained. Amounts of the compounds described herein which are therapeutically effective against specific diseases can also be determined through routine investigation.

The following examples are intended to illustrate, but not limit the invention. While they are typical of those that might be used, other procedures known to those skilled in the art may be alternatively employed. In the examples, the following abbreviations are used:

| | |
|---|---|
| EI | electron impact |
| FR | furosemide response |
| FT-IR | Fourier-transform infrared spectroscopy |
| HPLC | high performance liquid chromatography |
| MAP | mean arterial pressure |
| MDBK | Madin-Darby bovine kidney |
| MS | mass spectrometry |
| NMR | nuclear magnetic resonance |
| PBS | phosphate buffered saline |
| $R_n$ | natriuretic ratio |
| RP-HPLC | reverse-phase high performance liquid chromatography |
| SR | sample response |
| UNaV | urine concentration of sodium X urine volume per time |

Isolation of Natriuretic Compound

EXAMPLE 1

Human uremic urine was initially processed by ultrafiltration (3 kDa) and lyophilization, followed by isolation of the post-salt fraction from Sephadex G-25 gel filtration chromatography, following the procedure of Benaksas et al., Life Sci. 52, 1045–1054 (1993), the entire disclosure of which is herein incorporated by reference. See Table I (first purification step).

The crude material was further purified by one of two procedures. One procedure involved four sequential HPLC steps, and the second procedure included organic solvent extraction followed by up to five sequential HPLC steps. Table I summarizes the two methods.

TABLE 1

Summary of steps used in the chromatographic and extraction isolation procedures

| Purification Step | Chromatographic Method | Extraction Method |
|---|---|---|
| First | 3K ultrafiltration, lyophilization and G-25 | 3K ultrafiltration, lyophilization and G-25 |
| Second | 0.2 M pyridinium acetate pH 5.5/Methanol $C_{18}$ RP-HPLC | Sequential extraction with isopropanol/diethyl ether yielding soluble compounds |
| Third | 1st 0.2 M acetic acid/ methanol $C_{18}$ RP-HPLC | 1st 0.2 M acetic acid/ methanol $C_{18}$ RP-HPLC |
| Fourth | 2nd (modified) 0.2 M acetic acid/methanol $C_{18}$ RP-HPLC | 2nd (modified) 0.2 M acetic acid/methanol $C_{18}$ RP-HPLC[b] |
| Fifth | Isopropanol/hexane[a] | Isocratic 0.2 M acetic acid/methanol[c] |
| Sixth | | Isopropanol/hexane silica gel HPLC |
| Seventh | | 50 mM acetic acid/acetonitrile $C_{18}$ RP-HPLC[d] |

[a]Amount of resulting material of LLU-γ was so small that further purification was not pursued.
[b]LLU-γ was further purified by a chromatography step not used in the main purification scheme.
[c]This HPLC step was only used for isolation of LLU-α.
[d]LLU-α methyl ester was also purified using these HPLC conditions.

1. Chromatographic Isolation Method

A four-step sequential HPLC procedure was employed which was a modification of the procedure reported by Benaksas et al., noted above. The first $C_{18}$ RP-HPLC (Table 1, step 2) was performed on a Beckman Ultrasphere ODS column (10 μm; 21.2×150 mm) eluting at 6 mL/minute with a gradient of 0.2 M pyridinium acetate, pH 5.5 (A) and methanol (B) (80% A:20% B for 22 minutes, a linear gradient to 40% A:60% B over 48 minutes, a linear gradient to 100% B over 10 minutes). The column was washed with 70% toluene:30% methanol, then re-equilibrated at initial conditions for at least 20 minutes. This column wash method was implemented in every chromatography employing a methanol eluant. The eluant was monitored with a Beckman 166 UV detector at 290 nm. Eighty (80) one-minute fractions were collected and dried under reduced pressure in a centrifugal vacuum concentrator.

Based on bioassay evaluation (see Example 2, below) and chromatographic comparison of previous HPLC runs, fractions 50–80, were combined for the second RP-HPLC step (Table 1, third step). A Beckman Ultrasphere ODS ($C_{18}$) column (5 μm; 10×250 mm) was eluted at 2 mL/minute with a gradient of 0.2 M acetic acid (A), methanol (B) and 70% toluene: 30% methanol (C), (60% A:40% B for 5 minutes, a linear gradient to 50% A:50% B over 5 minutes, a linear gradient to 30% A:70% B over 55 minutes, a linear gradient to 100% B over 2 minutes, 100% B for 3 minutes, 100% C for 8 minutes, 100% B for 7 minutes). The eluant was monitored for fluorescence (exc. 310–410 nm; emm. 475–610 nm: Beckman 157 detector) and absorbance at 290 nm with a Beckman 168 diode array detector. Ultraviolet spectra were collected by diode array at 2 second intervals over the range of 202–390 nm. Eighty (80) one-minute fractions were collected.

As discussed in detail in Example 2, two natriuretically active isolates (LLU-α and LLU-γ) in particular were identified. The region encompassing the two natriuretically active isolates was pooled and rechromatographed using a modified acetic acid/methanol gradient for the third RP-HPLC (Table 1, fourth step). The solvents and column were the same as the second RP-HPLC above; however, the gradient was changed (60% A:40% B for 5 minutes, a linear gradient to 40% A:60% B over 5 minutes, a linear gradient to 30% A:70% B over 28 minutes, a linear gradient to 100% B over 2 minutes, 100% B for 3 minutes, 100% C for 8 minutes) and only fifty (50) one-minute fractions were collected.

During the first aqueous acetic acid-methanol RP-HPLC step (Table 1, third step), chromophore markers corresponding to natriuretically active materials could be identified when processing different batches of urine. By rechromatographing fractions 38–58 and 63–66 using a modified acetic acid-methanol method (Table 1, fourth step) employing a shorter gradient, the two natriuretically active marker chromophores, designated LLU-α and LLU-γ, reproducibly eluted at 27.8 and 35.4 minutes, respectively. This fourth purification step allowed consistent identification of natriuretically active crude isolates.

The LLU-α natriuretic isolate was subjected individually to normal phase chromatography on silica gel (Beckman Ultrasphere, 5 μm, 10×250 mm) eluting at 2 mL/minute with a hexane (B) isopropanol (A) gradient (6% A:94% B for 25 minutes, a linear gradient to 100% A over 30 minutes, 100% A for 20 minutes, a linear gradient to 6% A:94% B over 5 minutes and an equilibration period at 6% A:94% B for 35 minutes). Seventy (70) one-minute fractions were collected from this fifth purification step (Table 1). Fluorescence was monitored as described above. The wavelength monitored for each of the isolates was selected based upon its absorbance spectrum from the prior chromatogram. Chromatography of the first Isolate (LLU-α) was monitored at 295 nm and that of the second (LLU-γ) at 267 nm. Fractions exhibiting UV absorbance characteristic of LLU-α and LLU-γ were bioassayed (see below).

2. Extraction Method

Freeze-dried material obtained from the gel filtration chromatography was stirred with 9 volumes of isopropanol for 18 hours. The isopropanol solution was then removed and evaporated to dryness on a rotary evaporator under reduced pressure. The resulting thick, dark brown oil from the isopropanol soluble phase was weighed and then alternately stirred and sonicated for 6 hours and finally stirred for an additional 18 hours, with 10 volumes of diethyl ether. The ether solution was then decanted and 4 volumes of ether were added to the remaining insoluble material. After stirring for 72 hours, the ether solution was again decanted. Two volumes of deionized distilled water and 2 volumes of diethyl ether were added to the residue. After stirring for 2 hours, the ether phase was separated and the aqueous phase was washed three times with one volume of ether. The combined ether extracts were washed with saturated aqueous NaCl and water, and taken to dryness on a rotary evaporator under reduced pressure. The residue was redissolved in 95% ethanol and again taken to dryness.

The ether extraction residue was dissolved in 40% aqueous methanol and subjected to acetic acid-methanol RP-HPLC (Table 1, third step). The chromatographic region from LLU-α to LLU-γ, as identified by their characteristic UV spectra, was pooled, dried, re-suspended and chromatographed on the second modified acetic acid-methanol RP-HPLC (Table 1, fourth step). Only LLU-α and LLU-γ were detected after this chromatography step.

Isocratic acetic acid-methanol RP-HPLC (Table 1, fifth step) was then performed on LLU-α. Employing a Beckman Ultrasphere ODS ($C_{18}$) column (5 μm; 10×250 mm), LLU-α was eluted at 2 mL/minute with 45% 0.2 M acetic acid and 55% methanol for 35 minutes collecting seventy (70) half-minute fractions. The eluant was monitored for absorbance at 290 nm (diode array) and fluorescence. LLU-α was identified by its UV spectrum and subjected to silica gel HPLC (Table 1, sixth step).

The fractions containing LLU-α from the silica gel HPLC were pooled and subjected to another $C_{18}$ RP-HPLC step. In this seventh purification step (Table 1), a Beckman Ultrasphere ODS column (5 µm; 4.6×250 mm) was eluted at 1 mL/minute with a gradient of 50 mM acetic acid (A) and 45 mM acetic acid in acetonitrile (B) (85% A:15% B for 3 minutes, a linear gradient to 100% B over 42 minutes, 100% B for 5 minutes). The column was washed with 1:1 methylene chloride:acetonitrile for 5 minutes followed by re-equilibration at initial conditions for 16 minutes. Chromatography was monitored at 265 and 295 nm with the diode array detector. Fifty (50) half-minute fractions were collected staring at 10 minutes.

The extraction purification procedure increased the yield of isolated LLU-α by about 50%. In the chromatographic procedure, encompassing a total of five purification steps, less than 1 mg of LLU-α was obtained from about 105 g of lyophilized G-25 material (yield less than $9 \times 10^{-4}\%$). Approximately 1.8 mg of LLU-α resulted from the extraction procedure (seven purification steps) applied to about 155 g of lyophilized G-25 product (yield approximately $1.2 \times 10^{-3}\%$). The two additional RP-HPLC steps of this procedure led to essentially pure LLU-α. Likewise, the yield of LLU-α appeared to increase comparably.

LLU-α from the modified acetic acid-methanol RP-HPLC chromatography step (Table 1, fourth step) can be further purified using a method compatible for LC-MS. In this purification step, a Beckman Ultrasphere ODS column (5 µm, 4.6×250 mm) was eluted isocratically at 1 mL/minute with 0.1% trifluoroacetic acid, 40% acetonitrile, and 60% water for 30 minutes. LLU-γ from the previous chromatographic step elutes at 16.5 minutes. Between runs the column is washed with 0.1% trifluoroacetic acid in acetonitrile for 10 minutes, followed by reequilibration at initial conditions for 10 minutes. Chromatography was monitored at 265 and 230 nm with a diode array detector. LLU-γ was collected as a single fraction.

TABLE II

Chemical characteristics of the natriuretic LLUs

| | LLU-α | LLU-γ |
|---|---|---|
| Exact Mass | 264.1373 | ND[a] |
| Empirical Formula | $C_{15}H_{20}O_4$ | ND |
| UV Characteristics | λmax 205 nm<br>λmax 294 nm | λmax 220 nm<br>λmax 268 nm |
| Functional Groups Determined by IR | carboxyl<br>hydroxyl<br>aryl ether | ND |
| Physical Properties | Unstable in dilute Base<br>Unstable in $CDCl_3$ | Unstable when Purified<br>Very Unstable in Dilute Base |
| Reaction with $CH_2N_2$ | HNF-α methyl ester<br>$C_{14}H_{19}O_2CO_2CH_3$<br>MW 278.1515 +<br>Other Products | ND |

[a]ND: Not Determined

Isolated from early fractions of silica gel HPLC of LLU-α was the drug naproxen, which was being administered to some urine donors. Its identity was determined by NMR and verified by comparison with the NMR spectrum of commercial naproxen. Naproxen serves as an additional marker during the silica gel HPLC.

3. Treatment of LLU-α with $CH_2N_2$

Diazomethane was generated by treatment of 1-methyl-3-nitro-1-nitrosoguanidine (112 mg, 760 µmol) with 400 µL 50% KOH (aq). The diazomethane was distilled into 1 mL diethyl ether at −7° C. This solution was then added to 700 µg (2.6 µmol) LLU-α in 0.5 mL diethyl ether at 0° C. The reaction mixture was warmed to ambient temperature, then allowed to stand for 40 minutes. Solvent was removed under a stream of $N_2$ and the residue dissolved in 15% 45 mM acetic acid in acetonitrile/85% 50 mM acetic acid and subjected to the acetic acid-acetonitrile RP-HPLC purification step as described above (seventh step). The approximate yield of the ester was 53%. Methyl esterification of LLU-α followed by RP-HPLC yielded essentially pure LLU-α methyl ester. The methyl ester was synthesized to further the characterization of LLU-α. LLU-α methyl ester eluted as an apparently homogenous single peak from acetic acid—acetonitrile RP-HPLC. A total of approximately 0.9 mg of LLU-α methyl ester was isolated and subjected to chemical characterization by ultraviolet, infrared, $^{13}C$- and $^1H$-NMR and mass spectroscopy. The physical chemical characteristics, molecular weight and inferred molecular formula of both LLU-α and its methyl ester are listed in Table II.

Bioassays for Biological Activity

EXAMPLE 2

1. In Vivo Bioassay

The assay for natriuresis in conscious rats has been described previously (see Benaksas et al., above). The assay is briefly reiterated here. Female Sprague-Dawley (Harlan) rats (200–250 g) were cannulated in the femoral artery and vein for monitoring of mean arterial pressure (MAP) and Infusion of saline and samples, respectively. The bladder was catheterized for collection of urine in ten-minute periods. Furosemide (0.4 mg/kg bwt; 1 mg/mL in 0.17% saline) was infused as a positive control at the beginning of the sixth ten-minute period. The sample was infused at the beginning of the seventeenth ten-minute period. Urine was collected for another 150 minutes. The volume of the urine was determined gravimetrically and the $Na^+$ and $K^+$ concentrations determined with a Beckman E2A electrolyte analyzer. From these data the sodium excretion values (UNaV) were calculated.

The natriuretic response of a sample was normalized to the dose of furosemide infused. The not sodium excretion for the Infusion of furosemide or sample was calculated as follows. The median sodium excretion value (µmoles $Na^+$/10 minute period) for the five periods before infusion of furosemide or sample was used to establish a baseline value for the calculation of ΔUNaV (=µmoles $Na^+$ period−baseline µmoles $Na^+$) for administration of either furosemide or sample respectively. The sum of ΔUNaV for the four periods following infusion of furosemide was the net sodium excreted for furosemide, defined as FR. The sum of ΔUNaV for the fifteen periods following infusion of the sample was the net sodium excreted for the sample defined as SR. The natriuretic ratio $R_n$ (or normalized natriuretic response) of a sample was calculated by dividing SR by FR ($R_n$=SR/FR). A sample is considered natriuretically active if the $R_n$ value for that sample was greater than or equal to 0.67 (greater than 99% confidence limits).

Partially purified LLU-α from silica gel-HPLC (sixth purification step) was assayed for natriuretic activity utilizing the in vivo bioassay. It was active in the 4–8 μg/kg dose range and showed no activity at lower or higher doses (Table III). LLU-α is also active at 8 μg/kg when evaluated in the in vivo bioassay after being further purified on acetic acid/acetonitrile RP-HPLC (seventh step of extraction method).

TABLE III

Dose response of LLU-α present in fractions from the silica gel HPLC step of the extraction procedure from uremic urine

| Fraction | Dose (μg) | Natriuretic Response (R)[a] |
|---|---|---|
| 17 | 0.2 | −0.14 |
|  | 1 | 0.27 |
|  | 2 | 1.14 |
|  | 2 | 0.75 |
|  | 10 | 0.26 |
| 18 | 56.4 | 0.23 |
|  | 22.4 | 0.02 |
| 19 | 0.2 | 0.24 |
|  | 1 | 0.93 |
|  | 2 | −0.10 |
|  | 2 | 0.82 |
|  | 10 | 0.09 |
| 20 | 2 | 1.32 |
|  | 2 | 0.39 |
| 21 | 2 | −0.06 |
|  | 2 | 0.39 |

[a]Natriuretic ratio greater than 0.67 indicates that a sample is natriuretically active (99% confidence limits).

LLU-α and -γ when infused into the rat produced sustained natriuresis with no effect on blood pressure. LLU-γ has not been purified sufficiently to obtain a dose-response curve for natriuresis, owing to its instability. LLU-α displays a narrow and biphasic natriuretic dose-response curve (Table III). There was no detectable kaliuresis when LLU-α as infused. Some kaliuresis occurred after the infusion of LLU-γ, however, this was not always observed. Neither LLU-α nor -γ caused a significant Change in mean arterial pressure.

2. $Na^+/K^+$-ATPase Inhibition Assay

The assay in MDBK cells has been described previously (see Benaksas at al., above). The assay is described briefly here. Madin-Darby bovine kidney (MDBK) cells (ATCC:CCL22) were maintained in Dulbecco's Modified Eagle's Medium (DMEM) with 5% Fetal Bovine Serum and 5% Bovine Calf Serum in a 5% $CO_2$/95% humidified air atmosphere at 37° C. and split (1:2) once per week.

One day before the assay, cells were plated in a 96-well plate at a density of $5 \times 10^5$ cells/well in DMEM with serum. On the day of the assay the medium was removed and the cells washed with phosphate buffered saline (PBS) before addition of 100 μL of assay media (122 mM NaCl, 1.8 mM $CaCl_2$, 0.8 mM $MgSO_4$, 24 mM $NaHCO_3$, 1 mM sodium pyruvate, 25 mM glucose, 14 mM glycylglycine, 0.2% phenol red, 8 mM $Na_2HPO_4$ 1.15 mM $KH_2PO_4$, pH 8.0) and 100 μl of sample. The plate was preincubated for 30 minutes at 37° C., then chilled on ice for 10 minutes. To each well was added 0.15 μCi $^{86}$RbCl (Amersham) in 10 μL of assay media. The plate was then incubated at 37° C. for 10 minutes. A portion (100 μL) of the supernatant was counted with 0.5 mL of scintillation cocktail in a liquid scintillation counter. As a control for $Na^+/K^+$-ATPase inhibition, a dose response curve for ouabain in the range of $10^{-5}$–$10^{-8}$ M was obtained. Intra-experiment coefficient of variation for ouabain was 3–15%. Inhibition of $^{86}Rb^+$ uptake by samples was corrected for that uptake which was inhibitable by ouabain.

When LLU-α was assayed in the $Na^+/K^+$-ATPase inhibition assay it exhibited no inhibition in the range of 0.2–200 ng/well. Assay of crude LLU-γ obtained from the acetic acid-methanol RP-HPLC rechromatography step in the sodium pump inhibition assay showed no inhibition of the sodium pump.

Analytical Spectoscopy

EXAMPLE 3

In addition, spectroscopy other than UV was performed. $^{13}$C— and $^1$H-NMR spectra were recorded at 500.1357 MHz in deutero-Chloroform (99.9%) in a GN-500 spectrometer (General Electric). High resolution Electron-Impact (ED mass spectra with a resolution of 2000 were recorded at an ionization voltage of 70 eV, source temperature of 220° C. and introduction of sample by direct probe on a VG7070 EHF high resolution mass spectrometer. Fourier-transform infrared (FT-IR) spectroscopy was performed on a Nicolet 5DX with 4 wavenumber resolution.

The IR and $^{13}$C-NMR spectra of LLU-α provided evidence for the presence of a carboxylic acid group. This explained the tailing of LLU-α observed upon elution from isopropanol/hexane silica gel HPLC (sixth purification step). The presence of a carboxyl group was verified when the reaction of LLU-α with diazomethane resulted in a product that was less polar on RP-HPLC and had an exact mass 14 units greater than LLU-α as determined by MS (Table II). This is consistent with the formation of a methyl ester.

In the following synthesis examples, Examples 4–10 set forth general methods useful to produce a wide range of compounds within the scope of the invention. Examples 11–21 describe syntheses of specific compounds.

Synthesis of Racemic 6-hydroxychromanes

EXAMPLE 4

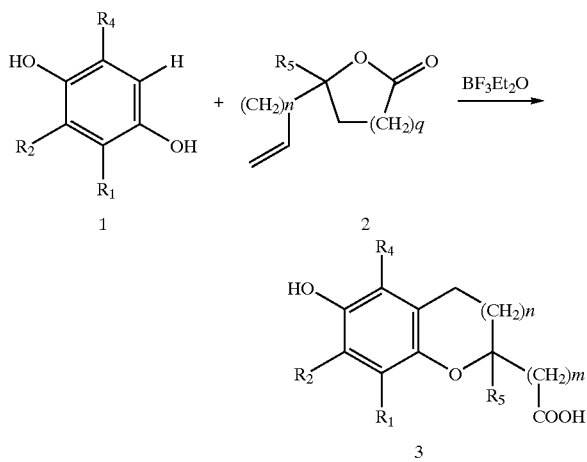

(formula C)

To a solution of hydroquinone 1 (0.01 mol) and a catalyst, preferably boron trifluoride diethyl etherate (0.016 mol) In an organic solvent, preferably dry dioxane (10 mL), is added vinyl lactone 2 (0.016 mol) in an organic solvent, preferably dry dioxane (5.0 mL) over 1–60 minutes, preferably 60 minutes, at 0–150° C., preferably 110° C., under an inert gas. The reaction mixture is stirred for 0 to 8 hours, preferably 0 hours, at the selected temperature, cooled to room temperature, and diluted with an organic solvent, preferably diethyl ether (200 mL) The reaction mixture is then washed with water (100 mL, 2×50 mL), dried over sodium sulfate ($Na_2SO_4$), and solvent is removed under reduced pressure to afford a brown oily residue. The residue is dissolved in alcohol, preferably methanol (30 mL), and the alcohol is then removed under reduced pressure. The brown oily liquid or semisolid is further purified by chromatography, preferably on silica gel, to afford pure racemic chroman derivative 3.

Synthesis of Racemic Chromans

EXAMPLE 5

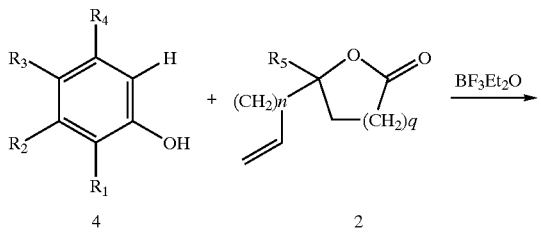
(formula D)

To a solution of phenol 4 (0.01 mol) and a catalyst, preferably boron trifluoride diethyl etherate (0.016 mol) in an organic solvent, preferably dry dioxane (10 mL), Is added vinyl lactone 2 (0.016 mol) In an organic solvent, preferably dry dioxane (5.0 mL) over 1–60 minutes, preferably 60 minutes, at 0–150° C., preferably 110° C., under an inert gas. The reaction mixture is stirred for 0 to 8 hours, preferably 0 hours, at the selected temperature, cooled to room temperature, and diluted with an organic solvent, preferably diethyl ether (200 mL). The reaction mixture is then washed with water (100 mL, 2×50 mL), dried over sodium sulfate ($Na_2SO_4$), and solvent is removed under reduced pressure to afford a brown oily residue. The residue is dissolved in alcohol, preferably methanol (30 mL), and the alcohol is then removed under reduced pressure. The brown oily liquid or semisolid is further purified by chromatography, preferably on silica gel, to afford pure racemic chroman derivative 5.

Synthesis of Chroman Methyl Esters

EXAMPLE 6

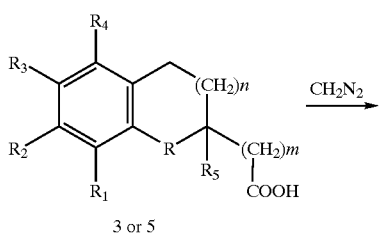
(formula E)

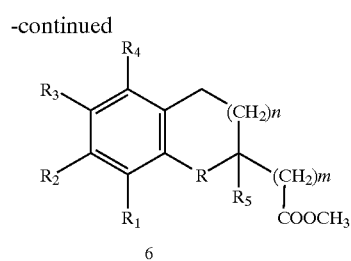
-continued

Chroman 3 ($R_3$=OH) or 5 (see Examples 4 and 5 above) (0.01 mol) is dissolved in methanol (30 mL), and a solution of diazomethane in ether is added at 0–5° C. until the yellow color of the diazomethane remains. The reaction mixture is left at room temperature for 2–5 hours, solvent is removed, and the desired product 6 is crystallized from a suitable organic solvent.

Synthesis of Chroman Esters

EXAMPLE 7

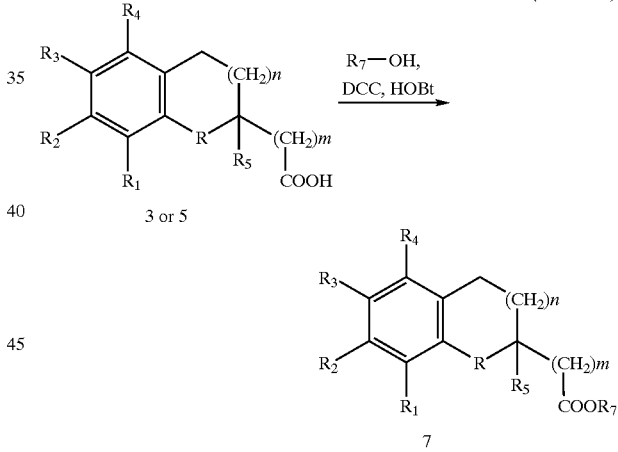
(formula F)

Chroman 3 ($R_3$=OH) or 5 (10 mmol) is dissolved in dry tetrahydrofuran (30 mL) with an alcohol $R_7$—OH (12 mmol), 1-hydroxybenzotriazole (10 mmol) and 1,3-dicyclohexylcarbodilmide (11 mmol) at 2–5° C. The reaction mixture is stirred at 2–5° C. for one hour and at 23° C. for one to 20 hours. Precipitated dicyclohexyl urea is filtered, solvent is removed under reduced pressure, and the residue is diluted with ethyl acetate (150 mL). The organic phase is washed with aqueous $KHSO_4$ (10%, 40 mL), water (50 mL) and saturated aqueous hydrogen carbonate (50 mL), and then dried over sodium sulfate. The solvent is removed under reduced pressure, and the residue is purified by chromatography, preferably silica gel, to afford pure racemic ester 7.

Synthesis of Chroman Amides

EXAMPLE 8

(formula G)

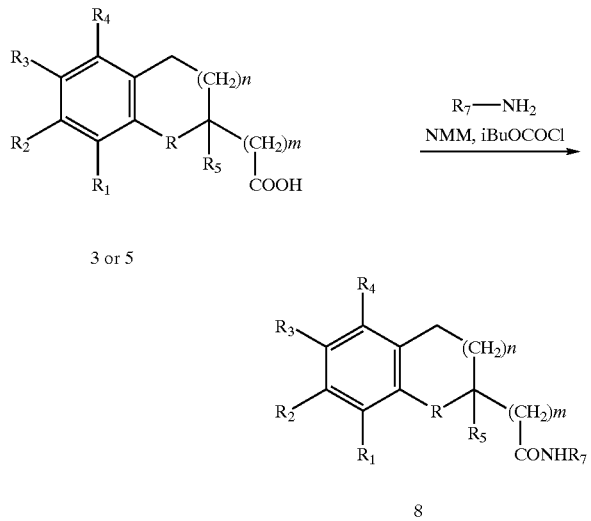

Chroman 3 ($R_3$=OH) or 5 (10 mmol) is dissolved in dry tetrahydrofuran (40 mL), and neutralized with N-methylmorpholine, isobutyl chlorocarbonate (10 mmol) is added, followed one minute later by a selected amine ($R_7$—$NH_2$ or $R_7R_8$—NH), or ammonia (11 mmol). The reaction mixture is allowed to reach room temperature. After stirring at room temperature for 1 hour, THF is removed under reduced pressure, and the residue is taken into ethyl acetate (250 mL). The ethyl acetate solution is successively washed with aqueous $KHSO_4$ (10%, 40 mL), water (50 mL), and saturated aqueous hydrogen carbonate (50 mL), and then dried over sodium sulfate. The solvent is removed under reduced pressure, and the residue is purified by chromatography, preferably silica gel, to afford pure racemic amide 8.

Synthesis of $R_4$ Chroman Esters

EXAMPLE 9

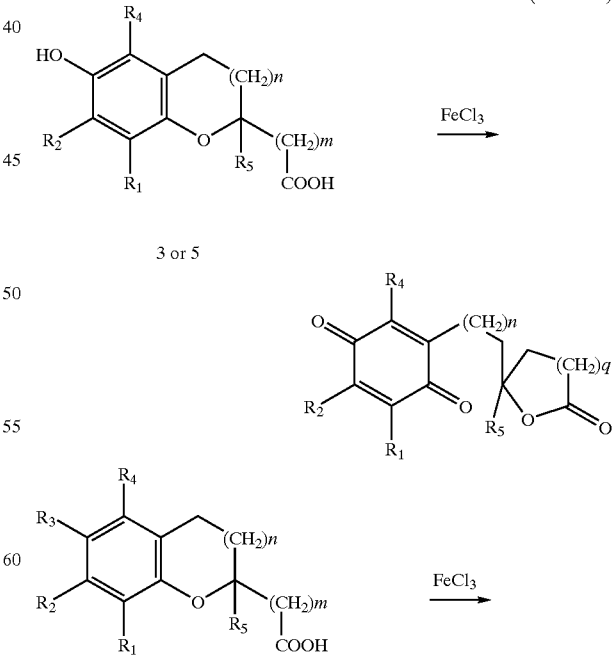

Method 1: Chroman 3 ($R_3$=OH) or 5 (10 mmol) is dissolved in pyridine (20 mL). and acid anhydride (30 mmol) is added at 5° C. The reaction mixture is left at room temperature for 18 hours, solvent is removed in vacuum, and the residue is dissolved in ethyl acetate (100 mL). washed with citric acid (10%, 30 mL). and water (30 mL). and dried over sodium sulfate. The solvent is removed and the residue is crystallized from ethyl acetate/hexane to afford ester 9.

Method 2: Chroman 3 ($R_3$=OH) or 5 (10 mmol) is dissolved in dry pyridine (50 mL) under nitrogen and cooled in an ice-water bath. Acyl chloride (10 mmol) is added via syringe over 15 minutes. Stirring is continued for 1 hour at room temperature. Pyridine is removed under reduced pressure, and the residue is dissolved in ethyl acetate (100 mL). The ethyl acetate phase is washed with water (2×40 mL). aqueous hydrochloric acid (0.05 M, 30 mL) and water (40 mL), and dried over sodium sulfate. The solvent is removed under reduced pressure, and the residue is purified by chromatography, preferably on silica gel, to afford ester 9.

Synthesis of Oxidized Chroman Derivatives

EXAMPLE 10

(formula J)

-continued

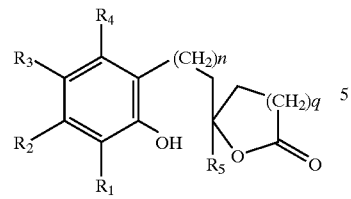

Chroman 3 or 5 (0.3 mmol) is dissolved in methanol (2.5 mL) in a flask. A ferric chloride solution is prepared by dissolving 1.0 g $FeCl_3$—$6H_2O$ in water (4.0 mL) and adding methanol (4.0 mL) The ferric chloride solution (2.5 mL) Is added to the flask at room temperature with vigorous stirring for 30 minutes in darkness. Methanol 13 removed in vacuum, and the residue Is dissolved In ether (70 mL) The ether solution is washed with water (3×20 mL) and dried over sodium sulfate, then the solvent is removed. The product is purified on an RP HPLC column ($CH_3CH/H_2O$ gradient) to afford a yellow-to-brown oily product.

Synthesis of Racemic 2,7,8-trimethyl-2-(β-carboxyethyl)-6-hydroxy Chroman (LLU-α)

EXAMPLE 11

(formula K)

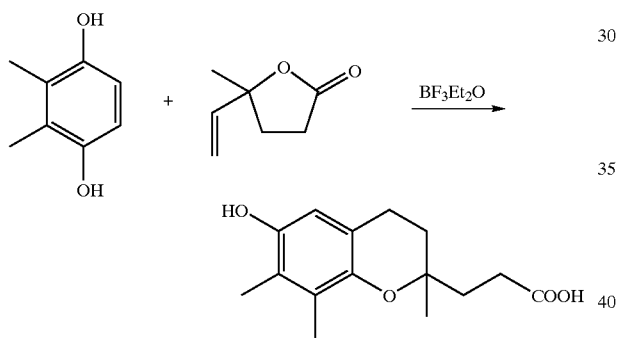

To a solution of 2,3-dimethyl-1,4-hydroquinone (0.01 mol) and boron trifluoride diethyl etherate (0.016 mol) in dioxane (10 mL, dried on sodium) in a flask was added γ-methyl-γ-vinylbutyrolactone (0.016 mol) in dioxane (5.0 mL) over 50 min at 110° C. (oil bath, reflux) under nitrogen. The reaction mixture was cooled to room temperature and diluted with ether (200 mL), then washed with water (100 mL, 2×50 mL) and dried over sodium sulfate. Ether was then removed under reduced pressure to afford a brown, oily residue. The residue was dissolved in methanol (30 mL) and solvent was removed under reduced pressure. The residue was redissolved in methanol (10 mL) and the flask was purged with nitrogen and stored at 5° C. for 20 hours. The resulting suspension was centrifuged, and the supernatant was removed. The remaining white solid (see Example 21, below) was suspended in aqueous 70% methanol (15 mL) and again centrifuged. The supernatant was combined with the previous supernatant, and methanol was removed in vacuum to afford a brown, oily liquid. The liquid was further purified by flash column chromatography on silica gel (eluent ethyl acetate/hexane/acetic acid, 500:300:1) to afford pure racemic 2,7,8-trimethyl-2-(β-carboxyethyl)-6-hydroxy chroman, which was crystallized from ether-hexane in a yield of 40%. M.P.: 147–148° C.

Synthesis of Racemic 2,5,7,8-tetramethyl-2-(β-carboxyethyl)-6-hydroxy Chroman

EXAMPLE 12

(formula L)

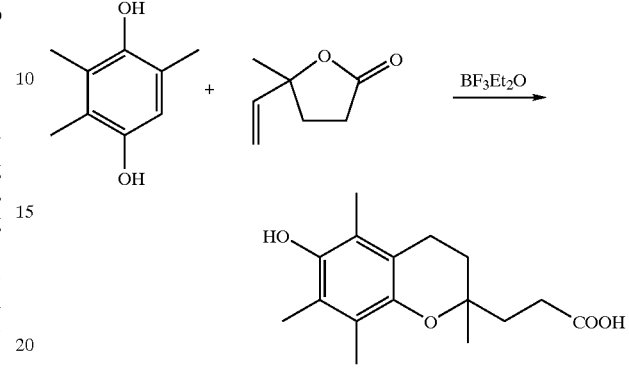

To a solution of 2,3,5-trimethyl-1,4-hydroquinone (0.01 mol) and boron trifluoride diethyl etherate (0.016 mol) in dioxane (10 mL, dried on sodium) in a flask was added γ-methyl-γ-vinylbutyrolactone (0.016 mol) in dioxane (5.0 mL) over 50 min at 110° C. (oil bath, reflux) under nitrogen. The reaction mixture was cooled to room temperature and diluted with ether (200 mL), then washed with water (100 mL, 2×50 mL) and dried over sodium sulfate. Ether was then removed in vacuum. The residue was dissolved in methanol (30 mL), and solvent was removed in vacuum. The brown, oily residue was dissolved in methanol (20 mL), and water was added until the solution became turbid (app. 20 mL), then the flask was purged with nitrogen and stored overnight in a refrigerator. The light yellow solid was filtered on a sinter funnel, washed with aqueous 50% methanol and dried in a dessicator. The product was further purified by flash column chromatography on silica gel (eluent ethyl acetate/hexane/acetic acid, 500:300:1) to afford pure racemic 2,5,7,8-tetramethyl-2-(β-carboxyethyl)-6-hydroxy chroman, which was crystallized from ether-hexane in a yield of 50%. M.P.: 173° C.

Synthesis of Racemic 2,5,7,8-tetramethyl-2-(β-carboxyethyl)-Chroman

EXAMPLE 13

(formula M)

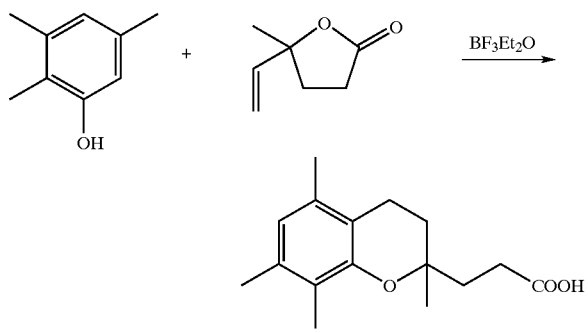

To a solution of 2,3,5-trimethylphenol (0.01 mol) and boron trifluoride diethyl etherate (0.016 mol) in dioxane (10 mL, dried on sodium) in a flask was added γ-methyl-γ-vinylbutyrolactone (0.016 mol) in dioxane (5.0 mL) via syringe pump over 50 min at 110° C. (oil bath, reflux) under nitrogen. The reaction mixture was cooled to room temperature and diluted with ether (200 mL), then washed with water (100 mL, 2×50 mL) and dried over sodium sulfate. Ether was then removed in vacuum. The residue was dissolved in methanol (30 mL) and solvent was removed in vacuum. The reaction mixture was purified by flash column chromatography on silica gel (eluent ethyl acetate/hexane, 1:1). Fractions containing the desired chroman were pooled, solvent was removed, and the compound was crystallized from ethyl acetate/hexane to afford a white crystalline product in a yield of 40%. M.P.: 148–149° C.

Synthesis of Racemic 2,7,8-trimethyl-2-(β-carboxyethyl)-chroman

EXAMPLE 14

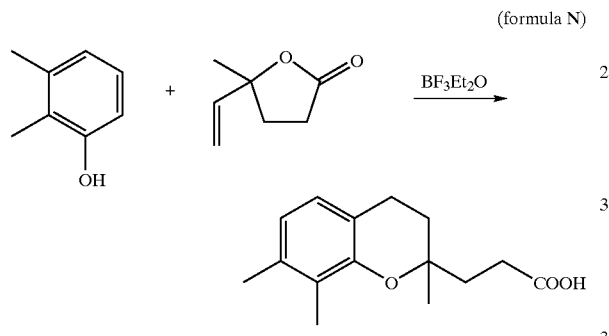

(formula N)

To a solution of 2,3-dimethylphenol (0.01 mol) and boron trifluoride diethyl etherate (0.016 mol) in dioxane (10 mL, dried on sodium) in a flask was added γ-methyl-γ-vinylbutyrolactone (0.016 mol) in dioxane (5.0 mL) via syringe pump over 50 min at 110° C. (oil bath, reflux) under nitrogen. The reaction mixture was cooled to room temperature and diluted with ether (200 mL) then washed with water (100 mL, 2×50 mL) and dried over sodium sulfate. Ether was then removed in vacuum. The residue was dissolved in methanol (30 mL), and solvent was removed in vacuum. The reaction mixture was purified by flash column chromatography on silica gel (eluent ethyl acetate/hexane, 1:1). Fractions containing the desired chroman were pooled, solvent was removed, and the compound was crystallized from ethyl acetate/hexane. M.P.: 93–94° C.

Synthesis of Racemic 4-methyl-6-(5,6-dimethylbenzohinoyl)-4-hexanolid

EXAMPLE 15

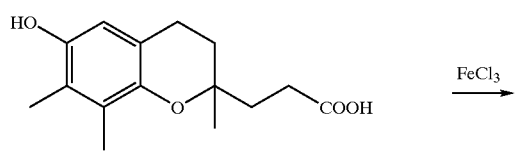

(formula O)

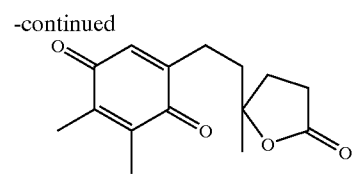

-continued

Racemic 2,7,8-trimethyl-2-(β-carboxyethyl)-6-hydroxychromane (100 mg) was dissolved in methanol (2.5 mL) in a flask. A solution of ferric chloride was prepared by dissolving 1.0 g FeCl$_3$—6H$_2$O in water (4.0 mL) and adding methanol (4.0 mL) The ferric chloride solution (2.5 mL) was added to the flask at room temperature with vigorous stirring in darkness for 30 minutes. Methanol was removed in vacuum, and the residue was dissolved In ether (70 mL). The ether solution was washed with water (3×20 mL) dried over sodium sulfate, and the solvent was removed. The product was purified on an RP HPLC column (CH$_3$CN/H$_2$O gradient) to afford a yellow-to-brown oily product in 60% yield.

Synthesis of Racemic 4-methyl-6-(3,5,6-trimethylbenzochinoyl)-4-hexanolid

EXAMPLE 16

(formula P)

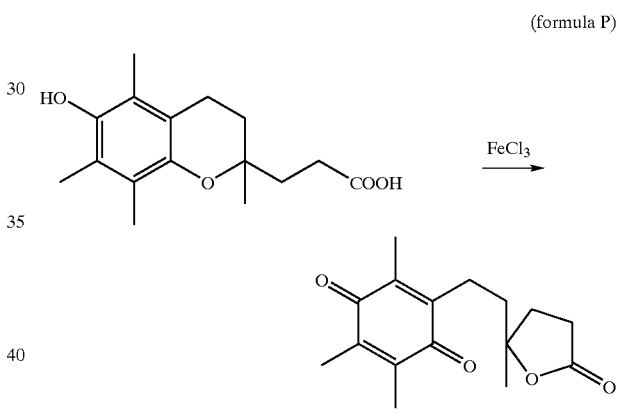

Racemic 2,5,7,8-tetramethyl-2-(β-carboxyethyl)-6-hydroxychromane (100 mg) was dissolved in methanol (2.5 mL) in a flask. The ferric chloride solution of Example 10 (2.5 mL) was added to the flask at room temperature with vigorous stirring in darkness for 30 minutes. Methanol was removed in vacuum, and the residue was dissolved in ether (70 mL) The ether solution was washed with water (3×20 mL) dried over sodium sulfate, and the solvent was removed. The product was purified on an RP HPLC column (CH$_3$CN/H$_2$O gradient) to afford a yellow-to-brown oily product in 60% yield.

Resolution of Racemic 2,7,8-trimethyl-2-(β-carboxyethyl)-6-hydroxy Chroman (LLU-α)

EXAMPLE 17

The resolution of (S) and (R)-enantiomers was carried out on an (S,S)-WHELK-O 1 column (Regis Technologies, Inc.) 250×4.6 mm, 1 mL/min, using as eluent isocratic 80% hexane:20% propanol:0.5% acetic acid. Fractions were monitored by UV spectroscopy, collected and dried under an argon stream. The enantiomers elute at 6.8 minutes and 8.7 minutes. Isolated LLU-α, when run on this system, elutes at 8.6 minutes.

Synthesis of (R)- and (S)-4-methyl-6-(5,6-dimethylbenzochinoyl)-4-hexanolid

EXAMPLE 18

(formula Q)

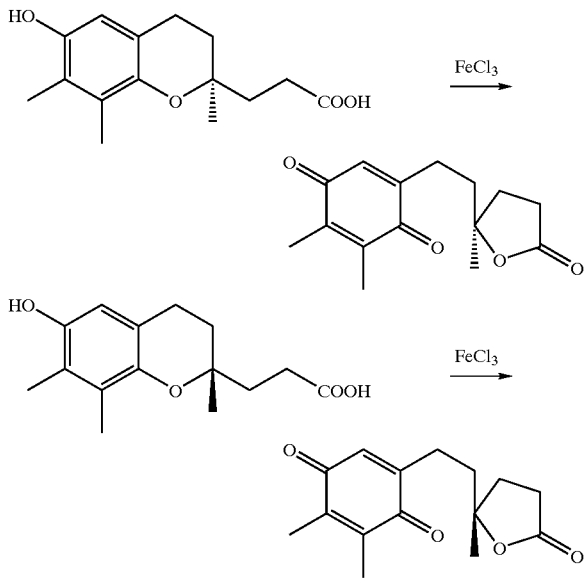

(R)-2,7,8-Trimethyl-2-(β-carboxyethyl)-6-hydroxy chroman 0 00 mg) (see Example 17) was dissolved in methanol (2.5 mL) and ferric chloride solution (2.5 mL) was added at room temperature with vigorous stirring for 30 minutes in darkness. Methanol was removed under reduced pressure, and the residue was dissolved in ether (70 mL). The ether solution was washed with water (3×20 mL) dried over sodium sulfate, and the solvent was removed. The product was purified by HPLC, using a Phenomenex column (SPHEREX 10 ODS, 250×21.2 mm) with $CH_3CN$—$H_2O$ 50:50 for 5 minutes, linear gradient to $CH_3CN$—$H_2O$ 90:10 in 30 minutes, linear gradient to 100% $CH_3CN$ in 5 minutes, flow rate 6 mL/min. Fractions containing the desired oxidation product were identified by UV spectroscopy. The fractions were pooled, and solvent was removed under reduced pressure to afford (R)-4-Methyl-6-(5,6-dimethylbenzochinoyl)-4-hexanolid as a yellow to brown oil.

The foregoing process was repeated using (S)-2,7,8-Trimethyl-2-(β-carboxyethyl)-6-hydroxy chroman (100 mg) to afford (S)-4-Methyl-6-(5,6-dimethylbenzochinoyl)-4-hexanolid as a yellow to brown oil.

Synthesis of Racemic 2,7,8-trimethyl-2-(β-carboxyethyl)-6-acetyl Chroman

EXAMPLE 19

(formula R)

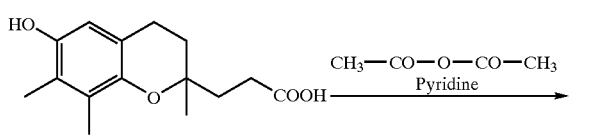

-continued

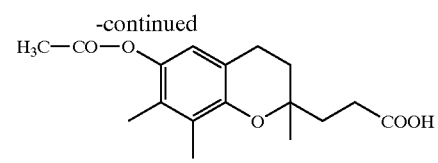

Racemic 2,7,8-Trimethyl-2-(β-carboxyethyl)-6-hydroxy chroman (500 mg) (see Example 11) was dissolved in pyridine (20 mL) at room temperature, and acetic anhydride (10 mL) was added. The solution was maintained at room temperature for 5 hours, solvent was removed under vacuum, methanol (4×10 mL) was added and then removed under reduced pressure. The residual oil was dissolved in ethyl acetate (150 mL) and the organic phase was washed with water (50 mL) aqueous HCl (1 N, 50 mL) and water (50 mL) then dried over sodium sulfate. Solvent was then removed, and the residual oily material was purified on -a silica gel column with hexane/ethyl acetate (1:1). The desired product crystallized from acetone/hexane, m.p. 105–107° C.

Synthesis of Racemic 2,7,8-trimethyl-2-(β-carboxyethyl)-6-acetyl Chroman Methyl Ester

EXAMPLE 20

(formula S)

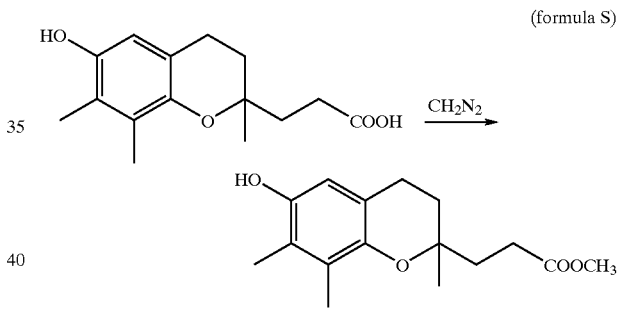

Racemic 2,7,8-Trimethyl-2-(β-carboxyethyl)-6-acetyl chroman (500 mg) (see Examples 11 and 19) was dissolved in methanol (10 mL), and etheral diazomethane was added until the yellow color of diazomethane remained. The solution was maintained at room temperature for 1 hour, solvent was removed, and the residue was purified on a silica gel column with hexane/acetone (3:1). The desired product crystallized from methanol/water, m.p. 87–88° C.

Synthesis of Benzodipyran Methyl Ester

EXAMPLE 21

(formula T)

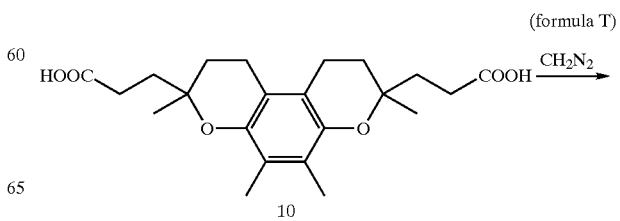

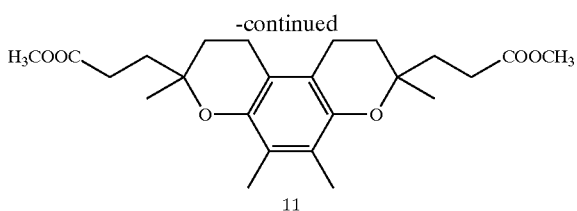

11

Benzodipyran derivative 10 (m.p. 225–227° C.) was isolated as a reaction byproduct from the synthesis of LLU-α (Example 11). Derivative 10 exists as a racemic mixture of a meso-(R,S) compound and a diastereomeric pair (R,R) and (S,S). Derivative 10 (1.0 g) was suspended in methanol (10 mL), and etheral diazomethane was added until the yellow color of diazomethane remained. The clear solution was maintained at room temperature for 1 hour, solvent was removed, and the residue was purified on a silica gel column with hexane/acetone (3:1). The desired product crystallized from hexane, m.p. 75–76° C.

Treatment and Prevention of High Blood Pressure

EXAMPLE 22

High blood pressure is a major contributory factor to cardiovascular related illness. The administration of a supplement according to the present invention, as detailed in the following example, will treat and prevent high blood pressure.

The blood pressure of a patient suffering from high blood pressure is determined by conventional methods. The patient is then given a daily dose of supplement (200–400 mg) containing a formulation of γ-tocopherol 75% (weight to weight) and LLU-α 25% (weight to weight). The daily course of supplementation is continued for a period of 9–12 months after which time the patient's blood pressure is again determined. After a period of 12 months, a reduction in blood pressure is observed. As a control, placebos or supplements containing equivalent amounts of α-tocopherol are provided to patients suffering from high blood pressure. The results of this study will demonstrate that supplementation with a formulation of γ-tocopherol and LLU-α will treat and prevent, high blood pressure in a patient suffering from this disease to a greater extent than supplementation with a placebo or an equivalent amount of α-tocopherol.

Treatment and Prevention of Thromboembolic Disease

EXAMPLE 23

Thromboembolic disease is a considerable problem for insulin-dependant diabetics, the elderly, and people suffering from cardiovascular disease. The administration of a supplement of the present invention, according to the example below, will treat and prevent thromboembolic disease.

Blood from a patient suffering from thromboembolic disease is drawn and a platelet aggregation assay, as known by one of skill in the art, is performed on the sample. (See Richardson and Steiner, *Adhesion of Human Platelets Inhibited by Vitamin E*, Chapter 24, *Vitamin E in Health and Disease*, Packer and Fuchs editors, Marcel Dekker Inc. Publishers 1993 pp. 297–311). The patient is then given a daily dose of supplement 200–400 mg containing a formulation of γ-tocopherol 75% (weight to weight) and LLU-α 25% (weight to weight). The daily course of supplementation is continued for a period of 2–4 weeks after which time the patient's blood is again drawn and platelet aggregation is determined. After a period of 4 weeks, a reduction in platelet aggregation will be observed. As a control, placebos or supplements containing equivalent amounts of α-tocopherol are provided to patients suffering from thromboembolic disease. The results of this study will demonstrate that supplementation with a formulation of γ-tocopherol and LLU-α will reduce platelet aggregation and thereby treat and prevent thromboembolic disease in a patient suffering from this malady better than supplementation with a placebo or an equivalent amount of α-tocopherol.

Reduction of Platelet Binding to Adhesive Proteins

EXAMPLE 24

Platelet aggregation and thromboembolic disease are related to the aberrant binding of platelets to adhesive proteins. By following the example disclosed below, platelet binding to adhesive proteins can be inhibited by supplementation of γ-tocopherol and LLU-α.

Blood from a patient suffering from thromboembolic disease is drawn and a platelet adhesion assay, as known by one of skill in the art, is performed on the sample. (See Richardson and Steiner, *Adhesion of Human Platelets Inhibited by Vitamin E*, Chapter 24 *Vitamin E in Health and Disease*, Packer and Fuchs editors, Marcel Dekker Inc. Publishers 1993 pp. 297–311). The patient is then given a daily dose of supplement 100–200 mg containing a formulation of γ-tocopherol 75% (weight to weight) and LLU-α 25% (weight to weight). The daily course of supplementation is continued for a period of 2–4 weeks after which time the patient's blood is again drawn and platelet adhesion is determined. After a period of 4 weeks, a reduction in platelet adhesion will be observed. As a control, placebos and supplements containing equivalent amounts of α-tocopherol can be provided to patients suffering from throboembolic disease. The results of this study will demonstrate that supplementation with a formulation of γ-tocopherol and LLU-α will reduce platelet binding to adhesive protein better than supplementation with a placebo or an equivalent amount of α-tocopherol.

Treatment and Prevention of Atherosclerosis (Arteriosclerosis)

EXAMPLE 25

Oxidized LDL is chemoattractant to circulating monocytes and inhibits macrophage mobility in the intima. Indiscriminate uptake of oxidatively modified LDL by scavenger receptors of macrophages results in cholesterol-laden foam cells and fatty-streak formation. These events, and the potential cytotoxicity of oxidized LDL, further promote the evolution of fatty streaks to a more advanced lesion and cardiovascular disease. In vitro indices of LDL oxidation are known in the prior art and can be adapted to determine the ability of a formulations of γ-tocopherol and LLU-α to prevent atheroscelerosis and cardiovascular disease. The following example provides one approach by which to treat and prevent atheroscelerosis cardiovascular disease.

Blood from a patient suffering from atheroscelerosis is drawn and the amount of oxidized LDL present in the sample is determined. (See Frei and Ames, *Relative Importance of Vitamin E in Antiperoxidative Defenses in Human Blood Plasma and Low-density Lipoprotein (LDL)*, Chapter 10 *Vitamin E in Health and Disease,* Packer and Fuchs editors, Marcel Dekker Inc. Publishers 1993 pp. 131–139). The patient is then given a daily dose of supplement 400–800 mg containing a formulation of γ-tocopherol 75% (weight to weight) and LLU-α 25% (weight to weight). The daily course of supplementation is continued for a period of 2–4 weeks after which time the patient's blood is again drawn and the amount of oxidized LDL present in the sample is determined. As a control, placebos or supplements containing equivalent amounts of α-tocopherol are provided to patients suffering from atheroscelerosis. The results of this study will demonstrate that supplementation with a formulation of γ-tocopherol and LLU-α will reduce the level of oxidized LDL in a patient and thereby treat and prevent. atherosclerosis (arteriosclerosis) and cardiovascular disease better than supplementation with a placebo or an equivalent amount of α-tocopherol.

Treatment and Prevention of Cancer

EXAMPLE 26

The antioxidant and nitrogen scavenger properties of γ-tocopherol and LLU-α can be used to treat and prevent cancer, as described below. The following example is based on an experimental methodology accepted by those of skill in the art to reflect anti-tumor effects in the human body. (See Elson, *Impact of Palm Oil on Experimental Carcinogenesis,* Chapter 39 *Vitamin E in Health and Disease,* Packer and Fuchs editors, Marcel Dekker Inc. Publishers 1993 pp. 533–545). Four groups of mice are used in the study: (1) control mice in which tumor formation is not induced but treatment with a formulation of γ-tocopherol 75% (weight to weight) and LLU-α 25% (weight to weight) is rendered; (2) control mice in which tumor formation is induced and treatment is not rendered; (3) experimental mice in which tumor formation is induced and treatment with γ-tocopherol 75% (weight to weight) is rendered; and (4) experimental mice in which tumor formation is induced and treatment with a formulation of γ-tocopherol 75% (weight to weight) and LLU-α 25% (weight to weight) is rendered. As a further control, mice in which tumor formation is induced are treated with varying concentrations of α-tocopherol so as to evaluate the relative effectivity of γ-tocopherol and the formulation of γ-tocopherol and LLU-α, as compared to α-tocopherol.

Mice which receive treatment with γ-tocopherol or a formulation of γ-tocopherol and LLU-α, as described above, are given 20 mg/kg of supplement for a period of 2–4 weeks. Tumor cells derived from a spontaneously arising mammary tumor are then injected into the thigh area of the experimental mice to induce tumor formation. Treatment with γ-tocopherol and the formulation of γ-tocopherol and LLU-α is continued according to the protocol above. After 21 days, the mean volume of tumors in the mice is determined and compared. The results of this study will demonstrate that the mean volume of tumors in the mice treated with γ-tocopherol and the formulation of γ-tocopherol and LLU-α, is less than the mean volume of tumors in the control mice in which tumor formation was induced but γ-tocopherol or the formulation of γ-tocopherol and LLU-α is not administered.

Reduction in the Formation of Free Radicals

EXAMPLE 27

A reduction in the formation of free radicals is thought to be essential to prevent cancer and cardiovascular disease. The following example provides an approach to evaluate the efficacy of supplementation with a formulation of γ-tocopherol and LLU-α for reducing the formation of free radicals.

Human excretion of breath pentane has been used in a number of human studies as a measure of free-radical reactions. (See Packer et al., *Significance of Vitamin E for the Athlete,* Chapter 34, *Vitamin E in Health and Disease,* Packer and Fuchs editors, Marcel Dekker Inc. Publishers 1993 pp. 465–471). The breath pentane is measured from two groups of human volunteers. The first group serves as the control for the study and is not supplemented with a formulation of γ-tocopherol and LLU-α. The second group is supplemented for 2–4 weeks (200–400 mg/day) with a formulation of γ-tocopherol 75% (weight to weight) and 25% (weight to weight) LLU-α. As another control, human volunteers supplemented with an equivalent amount α-tocopherol can be used. Both the control and experimental groups are subjected to exhaustive exercise and a measurement of breath pentane is taken shortly thereafter. The results will show that breath pentane, a measure of free-radical formation in the body, is reduced in humans who received supplementation with a formulation of γ-tocopherol and LLU-α as compared to a control group which received either no supplementation or supplementation with α-tocopherol.

Treatment and Prevention of Neuropathological Lesions

EXAMPLE 28

Vitamin E deficiency in animals is associated with axonal dystrophy that involves degeneration in the posterior cord and in the gracile and cuneate nuclei. Humans who suffer from malabsorption syndromes that are associated with decreased absorption or transport of vitamin E develop similar neurological symptoms including hyporflexia, gait disturbances, decreased sensitivity to vibration and proprioception and opthalmoplegia. Neuropathological lesions, including axonal degeneration of the posterior cord and the gracilis nucleus in humans are comparable with those found in animals deficient in vitamin E. Rats suffering from vitamin E deficiency can be used to determine the therapeutic benefits of supplemention with a formulation of γ-tocopherol and LLU-α, according to the following example, for the treatment and prevention of neurological conditions.

Rats are maintained on a vitamin E depleted diet for a period of 8 weeks so that neuropathological lesions are allowed to develop. One group of vitamin E deficient rats is continued on the vitamin E depleted diet without vitamin E supplementation during the course of the study and serves as a control. A second control consists of vitamin E deficient rats maintained on a vitamin E depleted diet but supplemented with 20 mg/kg of α-tocopherol. The experimental group of vitamin E deficient rats is treated with either 20 mg/kg of γ-tocopherol or a formulation 75% (weight to weight) of γ-tocopherol and 25% (weight to weight) LLU-α for a period of 2–4 weeks. The rats are then sacrificed and the presence of neuropathological lesions is determined by methods known in the art. The results of this study will demonstrate that supplementation with a formulation of γ-tocopherol and LLU-α will treat and prevent the formation of neuropathological lesions associated with vitamin E deficiency better than supplementation with α-tocopherol or no supplementation at all.

Modulation of Immune System Response

EXAMPLE 29

The main role of vitamin E in enhancing immune response is believed to involve the prevention of lipid perioxidation of cell membranes. The rapidly proliferating cells of the stimulated immune and phagocytic systems are particularly prone to perioxidative damage by free radicals, peroxides, and superoxides. Vitamin E supplementation has been shown to modulate the immune response of mammals as evidenced by a reduction in $PGE_2$ production, an increase in mitogenic response, an increase in IL-2 production, and the induction of delayed-type hypersensitivity (DTH). (See Meydani and Tengerdy, *Vitamin E and Immune Response*, Chapter 40, *Vitamin E in Health and Disease*, Packer and Fuchs editors, Marcel Dekker Inc. Publishers 1993 pp. 549–561). An improvement in immune response after supplementation with a formulation of γ-tocopherol and LLU-α are determined by measuring the reduction of $PGE_2$ and the increase in IL-2 production in mice, according to the following example.

A first group of mice, the control group, does not receive treatment with γ-tocopherol or a formulation of γ-tocopherol and LLU-α. To compare the therapeutic benefits of a formulation of γ-tocopherol and LLU-α with α-tocopherol, a control group which receives treatment with α-tocopherol is used. A second group of mice, the experimental group, receives treatment with a formulation of γ-tocopherol and LLU-α. Treatment consists of 40 mg/kg of a formulation of γ-tocopherol 75% (weight to weight) and LLU-α 25% (weight to weight) for a period of 8 weeks. Shortly after the treatment phase, the control and experimental groups are administered an antigen which illicits an immune response. Next, the $PGE_2$ production and IL-2 production is determined by conventional methods. The results of this study will demonstrate that mice which received treatment with a formulation of γ-tocopherol and LLU-α exhibit a lower level of $PGE_2$ and an increase in IL-2 production as compared to control mice which received either α-tocopherol supplementation or no supplementation at all.

Although the invention has been described with reference to the presently preferred embodiment, it should be understood that various modifications can be made without departing from the spirit of the invention. Accordingly, the invention is limited only by the following claims. All references cited herein are hereby expressly incorporated by reference.

What is claimed is:

1. A method of preventing or treating a disease caused by oxidation in vivo by administering a pharmacologically effective amount of at least one compound selected from the group consisting of: (1) 2,5,7,8-tetramethyl-2-(β-carboxyethyl)-6-hydroxychromane, a pharmacologically acceptable salt thereof or a pharmacologically acceptable hydrate thereof and (2) 2,7,8-trimethyl-2-(β-carboxyethyl)-6-hydroxychromane, a pharmacologically acceptable salt thereof or a pharmacologically acceptable hydrate thereof.

2. The method of claim 1, wherein the disease is caused by oxidated low density lipoprotein (LDL).

3. The method of claim 1, wherein the disease is arteriosclerosis.

* * * * *